(12) United States Patent
Gill et al.

(10) Patent No.: US 10,007,754 B2
(45) Date of Patent: Jun. 26, 2018

(54) ANALYSIS OF DNA SAMPLES

(71) Applicant: LGC Limited, Teddington, Middlesex (GB)

(72) Inventors: Peter David Gill, Solihull (GB); Jonathon Paul Whitaker, Solihull (GB); John Simon Buckleton, Solihull (GB)

(73) Assignee: LGC LIMITED, Teddington, Middlesex (GB)

( * ) Notice: Subject to any disclaimer, the term of this patent is extended or adjusted under 35 U.S.C. 154(b) by 777 days.

(21) Appl. No.: 13/914,174

(22) Filed: Jun. 10, 2013

(65) Prior Publication Data

US 2014/0162253 A1 Jun. 12, 2014

Related U.S. Application Data

(63) Continuation of application No. 13/163,147, filed on Jun. 17, 2011, which is a continuation of application No. 12/643,723, filed on Dec. 21, 2009, which is a continuation of application No. 12/042,894, filed on Mar. 5, 2008, which is a continuation of application No. 10/977,698, filed on Oct. 29, 2004, which is a continuation of application No. 09/834,822, filed on Apr. 13, 2001.

(30) Foreign Application Priority Data

Apr. 15, 2000 (GB) .................................. 0009294.0

(51) Int. Cl.
*G01N 33/48* (2006.01)
*G06F 19/22* (2011.01)
*G06F 19/18* (2011.01)

(52) U.S. Cl.
CPC .............. *G06F 19/22* (2013.01); *G06F 19/18* (2013.01)

(58) Field of Classification Search
CPC ...................................................... G06F 19/22
USPC .......................................................... 702/19
See application file for complete search history.

(56) References Cited

U.S. PATENT DOCUMENTS

| | | | |
|---|---|---|---|
| 5,710,028 A | 1/1998 | Navot et al. | |
| 6,713,253 B1 | 3/2004 | Duff et al. | |
| 2002/0007248 A1 | 1/2002 | Gill et al. | |

FOREIGN PATENT DOCUMENTS

| | | |
|---|---|---|
| GB | 2 312 747 | 11/1997 |
| WO | WO 93 25563 | 12/1993 |
| WO | WO 01/79541 A2 | 10/2001 |
| WO | WO 01/89541 A2 | 10/2001 |
| WO | WO 03/083138 A | 10/2003 |

OTHER PUBLICATIONS

Bill, M. et al., "Pendulum—a-guideline-based approach to the interpretation of STR mixtures," Forensic Science International, vol. 148, No. 2-3, Mar. 10, 2005, pp. 181-189.
Brownie, et al., "The Elimination of Primer-Dimer Accumulation in PCR," Nucleic Acids Research, vol. 25, No. 16, pp. 3235-3241, 1997.
Clayton T.M., et al., "Analysis and Interpretation of Mixed Forensic Strains Using DNA STR Profiling," Forensic Science International, vol. 91, 1998, pp. 55-70.
Curran et al. "Interpretation of repeat measurement DNA evidence allowing for multiple contributors and population substructure," Forensic Science International, vol. 148, 2005, pp. 47-53.
Curran, J.M. et al., "Interpreting DNA Mixtures in Structured Populations," Journal of Forensic Science, vol. 44, No. 5, Sep. 1999, pp. 987-995.
Gill et al., "An investigation of the rigor of interpretation rules for STRs derived from less than 100 pg of DNA," Forensic Science International (2000) 112: 17-40.
Gill, "An Assessment of the Utility of Singlenucleotide Polymorphisms (SNPs) for Forensic Purposes," International Journal of Legal Medicine, vol. 114, Apr. 2001, pp. 204-210.
Gill, et al., "Interpreting Simple Mixtures Using Allele Peak Areas," Forensic Science International, vol. 91, Jan. 9, 1998, pp. 41-53.
Gill, P., "Role of Short Tandem Repeat DNA in forensic casework in the Uk—past, present, and future perspectives," Biotechniques, vol. 32, No. 2, Feb. 2002, pp. 226-385.
Gill, P., et al., "Development of guidelines to designate alleles using an STR multiplex system," Forensic Science International, vol. 89, No. 3, 1997, pp. 185-187.
Gill, P., et al., "Interpretation of simple mixtures of when artifacts such as stutters are present: With special reference to multiplex STRs used by the Forensic Science Service,." Forensic Science International, vol. 95, No. 3, Aug. 12, 1998, pp. 213-224, XP001027029.
Gill, Peter, et al., "Automated short tandem repeat (STR) analysis in forensic casework: A strategy for the future," Electrophoresis, vol. 16, No. 9, 1995, pp. 1543-1552, XP001027034.
Heath, et al., "Universal Primer Quantitative Fluorescent Mutiplex (UPQFM) PCR: A Method to Detect Major and Minor Rearrangements of the Low Density Lipoprotein Receptor Gene," Med Genet 2000; 37:272-280, 1999.
Hoogendoorn et al., "Genotyping Single Nucleotide Polymorphisms by Primer Externsion and High Performance Liquide Chromatography," Human Genetics, Berlin, DE, vol. 104, pp. 89-93, 1999.
Newton, et al., "Analysis of Any Point Mutation in DNA. The Amplification Refractory Mutation System (ARMS) ," Nucleic Acids Research, vol. 17, No. 7, pp. 2503-2516, 1989.

(Continued)

*Primary Examiner* — Jerry Lin
(74) *Attorney, Agent, or Firm* — Merchant & Gould P.C.

(57) ABSTRACT

The invention provides an improved method for obtaining information about DNA analysis of samples of uncertain origin by establishing the likelihood that they arose in certain manners compared with other possible manners. In this way all of the analysis information is taken into account and likelihood ratios are provided to express the results. The invention is particularly useful in analyzing small DNA samples or DNA samples where the contribution from one or more sources is small.

15 Claims, 12 Drawing Sheets

(56) References Cited

OTHER PUBLICATIONS

Old, "Detection of Mutations by the Amplification Refractory Mutation System (Arms)," *Methods in Molecular Biology*, US, Humanna Press, Inc., Clifton, NJ, vol. 9, pp. 77-84, 1991.

Paranavitana, "Non-radioactive Detection of K-ras mutations by Nested Allele Specific PCR and Oligonucleotide Hybridization," *Molecular and Cellular Probes* 12, 309-315, 1998.

Shuber, et al., "A Simplified Procedure for Developing Mutiplex PCRs," *Genome Research*, Cold Spring Harbor Laboratory Press ISSN, 5:488-493, 1995.

Wang et al., "Large-scale Identification, Mapping, and Genotyping of Single-nucleotide Polymorphisms in the Human Genome," *Science, US, American Association for the Advancement of Science*, vol. 280, pp. 1077-1082, 1998.

Weir, et al., "Interpreting DNA Mixtures," *Journal of Forensic Science*, vol. 42, No. 2, Mar. 1997, pp. 213-222.

Wu, et al., "Allele-specific Enzymatic Application of β-globin Genomic DNA for Diagnosis of Sickle Cell Anemia," PNAS, vol. 88, pp. 2757-2760, 1989.

Puch-Solis, "Statistical Specification of DNA LiRa v1.2," LGC Forensics (2015).

Haned et al., "LRmix Studio 2.0 user manual," (2015).

Balding, "Evaluation of mixed-source, low-template DNA profiles in forensic science," PNAS, (2012).

Puch-Solis et al., "Evidential evaluation of DNA profiles using a discrete statistical model implemented in the DNA LiRa software," Forensic Science International: Genetics, (2014).

Gill, P. et al., "DNA commission of the International Society of Forensic Genetics: Recommendations on the evaluation of STR typing results that may include drop-out and/or drop-in using probabilistic methods", Forensic Science International: Genetics, 6: 679-688 (2012).

"A Billion to one: How new DNA method was used for the first time to catch a killer", Express & Star, 7 pages (2016), https://www.expressandstar.com/news/crim/2016/09/20/ronald-smith-murder-how-new-dna-method-was-used-for-the-first-time-to-catch-a-killer/.

SET A

SET B

SET C

SET D

| Mj | P(Mj) | $R_1(12)$ | $R_2(16)$ | $R_3(12,16)$ | Products |
|---|---|---|---|---|---|
| 12 12 | $f_{12}^2$ | $p(\bar{D})p(\bar{C})$ | $p(D)p(\bar{C})f_{16}$ | $p(\bar{D})p(C)f_{16}$ | $p(\bar{D})^2 p(C)p(\bar{C})p(D)p(C)^2 f_{12}^2 f_{16}^2$ |
| 12 16 | $2f_{12}f_{16}$ | $p(D)p(\bar{C})p(\bar{D})$ | $p(D)p(\bar{C})p(\bar{D})$ | $p(\bar{D})^2 p(\bar{C})$ | $2p(\bar{D})^4 p(\bar{C})^3 p(D)^2 f_{12} f_{16}$ |
| 16 16 | $f_{16}^2$ | $p(D)p(C)f_{12}$ | $p(\bar{D})p(\bar{C})$ | $p(\bar{D})p(C)f_{12}$ | $p(\bar{D})^2 p(C)p(D)p(C)^2 f_{12}^2 f_{16}^2$ |
| | | | | | Denominator=sum of above |

FIG. 3

| $M_j$ | $P(M_j)$ | $R_1=abc$ | $R_2=ac$ | Products |
|---|---|---|---|---|
| $ab$ | $2f_af_b$ | $p(\overline{D})^2p(C)f_cp(\overline{St})^2$ | $p(\overline{D})p(D)p(C)f_cp(\overline{St})^2$ | $2f_af_bf_c^2p(\overline{D})^3p(D)p(C)^2p(\overline{St})^4$ |
| $ac$ | $2f_af_c$ | $p(\overline{D})^2p(\overline{St})[p(St)p(\overline{C})+p(\overline{St})p(C)f_b]$ | $p(\overline{D})^2p(\overline{C})p(\overline{St})^2$ | $2f_af_cp(\overline{D})^4p(\overline{C})p(\overline{St})^3[p(St)p(\overline{C})+p(\overline{St})p(C)f_b]p(\overline{D})^2p(\overline{St})^4$ |
| $bc$ | $2f_bf_c$ | $p(\overline{D})^2p(C)f_ap(\overline{St})$ | $p(\overline{D})p(D)p(C)f_ap(\overline{St})^2$ | $2f_a^2f_bf_cp(\overline{D})^3p(D)p(C)^2p(\overline{St})^3$ |

FIG. 4

| $p(D)$ | Amelo | D19S433 | D3S1358 | D8S1179 | HUMTH01 | HUMVWFA31/A | D2S13381 | HUMFIBRA (FGA) | D16S539 | D18S51 | D2S1338 | Mean |
|---|---|---|---|---|---|---|---|---|---|---|---|---|
| $p(D_{Ha})$ | 0.40 | 0.60 | 0.50 | 0.56 | | 0.62 | | | | | | 0.54 |
| $p(D_{He})$ | | | | | 0.32 | | 0.36 | 0.28 | 0.44 | 0.32 | 0.20 | 0.32 |
| $p(D_{Ha2})$ | | | | | 0.64 | | 0.52 | 0.68 | 0.46 | 0.56 | 0.70 | 0.59 |

FIG. 10

ANALYSIS OF DNA SAMPLES

This application is a Continuation of Ser. No. 13/163,147, filed 17 Jun. 2011, which is a Continuation of Ser. No. 12/643,723, filed Dec. 21, 2009, which is a Continuation of Ser. No. 12/042,894, filed Mar. 5, 2008, which is a Continuation of Ser. No. 10/977,698, filed Oct. 29, 2004, which is a Continuation of Ser. No. 09/834,822, filed Apr. 13, 2001 and which claims benefit of Serial No. 0009294.0, filed Apr. 15, 2000 in the United Kingdom and which applications are incorporated herein by reference. To the extent appropriate, a claim of priority is made to each of the above disclosed applications.

This invention concerns improvements in and relating to analysis of DNA samples, particularly, but not exclusively, in relation to analysis of DNA samples formed of only a few cells.

A variety of situations, including forensic investigation, make it desirable to be able to obtain information about DNA in a sample and express how reliable that information is. There are particular problems in analysing small DNA samples and as such present techniques tend to involve a substantial level of amplification for the DNA followed by examination of the results by an expert in interpreting such investigations. Such examinations are extremely complex. The expert generally deploys his knowledge to determine which of the individual results can be relied upon and which should be discounted when reaching the overall result. This approach by its very nature is subjective and only makes use of some of the actual individual results obtained when making a determination. Additionally the need for an expert analysis introduces a restriction on who can perform the review, and hence on the cost and time taken to perform the review.

The present invention has amongst its aims to provide a technique in which all information in an analysis result for a DNA sample is compared with results for reference samples with a view to determining a probability of a match between the test sample and each of the reference samples by calculating likelihood ratios. The present invention has amongst its aims to provide a technique in which all of the information obtained from the analysis of the DNA sample is used in the determination of the results. The present invention has amongst its aims to provide a technique in which the impact of potential spurious results can be quantified. The present invention has amongst its aims a technique for validating approximations which may be made in the analysis of DNA sample. The present invention has amongst its aims the provision of a system which can be operated successfully by competent but non-expert persons. The present invention has amongst its aims the provision of providing a technique whereby complex samples that comprise mixtures may be analysed.

According to a first aspect of the invention we provide a method of comparing one or more reference samples of DNA with at least part of a test sample of DNA, the method including:— the determination of the identity of the alleles present at a locus for the DNA in the test sample, the determination defining an individual test result, the determination being performed for a plurality of loci to give a plurality of individual test results, the consideration of one of the plurality of individual test results against the individual reference result of one of the reference samples for the respective loci, the consideration involving an expression of the probability that the individual reference result for that locus could lead by various possible routes to the individual test result for that locus, the possible routes to the individual test result including routes where spurious information contributes to the individual test result;

the consideration being repeated for a plurality of loci, the expressions of probability that the individual reference result could lead to the individual test result for the plurality of loci being combined to give an expression of the probability that the test sample matches the reference sample by calculating a likelihood ratio.

The reference samples may be from known individuals and/or associated with other known factors, such as locations, items or events. Each reference sample is preferably represented by one or more individual stored results. Each reference sample is preferably represented by 8 or more individual stored results. Each reference sample is preferably represented by individual stored results which provide the allele identity or allele identities for a given locus.

The reference samples may be stored in a database. The database may be updated periodically. New reference samples may be added to the database. Additional individual results may be added to existing reference samples.

The test sample may be from a known individual and/or be associated with one or more other known factors, such as a location, item or event the sample was recovered from. The test sample may be from one or more sources. One or more of the sources of the sample may be known or predicted.

The identity of the alleles at one or more of the loci of the reference sample and/or test sample may be determined by short tandem repeat based investigation.

Whilst the technique is applicable to all loci, the loci for which allele identity is determined may particularly be selected to include one or more of HUMVWFA31, HUMTH01, D21S11, D18S51, HUMFIBRA, D8S1179, HUMAMGXA, HUMAMGY, D3S1358, HUMVWA, D16S539, D2S1338, Amelogenin, D8S1179, D21S11, D18S51, D19S433, HUMTH01, HUMFIBRA/FGA. The loci selected may particularly be each of D3S1358, HUMVWA, D16S539, D2S1338, Amelogenin, D8S1179, D21S11, D18S51, D19S433, HUMTH01, HUMFIBRA/FGA.

An individual test result is preferably the allele or alleles detected for that given locus and/or the apparent alleles detected when that locus is considered. The individual test result may comprise 0 to 50 alleles, but more usually comprises 0 to 32 alleles. The individual test result may thus include the homozygous or heterozygous alleles of the test sample's source, homozygous and/or heterozygous alleles from DNA contamination of the test sample and/or stutters of these and/or other amplification artifacts.

The consideration is preferably provided for between 1 and 25 loci and more preferably between 1 and 16 loci. Preferably an equivalent consideration process is provided for each locus.

The consideration preferably involves the determination of a likelihood ratio. The likelihood ratio preferably accounts for the probability of the individual sample result arising from the individual reference result against the probability of the individual sample result arising from other than the individual reference result.

The consideration may involve the probability of the individual test result arising given that individual reference result, including through spurious information occurrence, divided by the probability of the individual test result arising from other than the individual reference result in any way, including through spurious information occurrence. Preferably the consideration may involve the probability of the individual test result arising given that individual reference result, including through spurious information occurrence, divided by the product of the probability of the individual test result arising from other than the individual reference result, including through spurious information occurrence, and the frequency of that individual stored result in a population. More preferably the consideration may involve the probability of the individual test result arising that individual reference result, including through spurious information occurrence, for each individual test result, divided by the product of the probability of the individual test result arising from other than the individual reference result, including through spurious information occurrence, and the frequency of that individual reference result in a population, for each individual test result.

Complex likelihood ratios may be formulated in order to evaluated a mixture. In such a case, for a known and unknown contributor scenario, the likelihood ratio may be the probability of the individual test result arising from an individual stored result, and other than the individual stored result divided by the probability of the individual test result arising from other than the individual stored result and from other than the individual stored result.

The consideration may incorporate an assessment of spurious alleles (either stutters of contaminants or other artefacts), that are factored into the probability calculations. In addition, the probability of observation of alleles may be calculated from the frequency of occurrence in relevant populations and used in the consideration. The frequency of occurrence may be derived from an Afro-Caribbean, Asian and white Caucasian population. The consideration may include an adjustment to probabilities to account for inbreeding.

The consideration may take into account more than one route involving spurious information and/or more than one type of spurious information.

Where contamination is necessary to lead to the individual test result the probability preferably includes a probability term for spurious allele occurrence.

Where contamination must not occur to lead to the individual test result the probability preferably includes a probability term for spurious allele non-occurrence.

Where stutter is necessary to lead to the individual test result the probability preferably includes a probability term for stutter occurrence.

Where stutter must not occur to lead to the individual test result the probability preferably includes a probability term for stutter non-occurrence.

Where allele dropout is necessary to lead to the individual test result the probability preferably includes a probability term for allele dropout occurrence.

Where allele dropout must not occur to lead to the individual test result the probability preferably includes a probability term for allele dropout non-occurrence.

Where artifact reporting is necessary to lead to the individual test result the probability preferably includes a probability term for artifact reporting occurrence.

Where artifact reporting must not occur to lead to the individual test result the probability preferably includes a probability term for artifact reporting non-occurrence.

In the following definitions of probability functions, the probability function may include, and ideally is a multiple of, the probability of that possible identity occurring in a population.

Reference to a population may include the world population, a representative sample there of, an arbitrary selected population, pseudo-random population, database content or other population.

Where the individual test result has two alleles, the individual reference result has two alleles and the individual reference result is a match for the individual test result in respect of both alleles, then the probability function may involve, with respect to the alleles of the individual reference result, one or more of:—a probability term for one or both alleles that drop out did not occur; a probability term for one or both alleles that stutter did not occur; a probability term for one or both alleles that spurious alleles did not occur, a probability term for one or both alleles that other artifacts did not occur. Where the individual test result has two alleles, one being one repeat unit less (or 4 bases less for a tetrameric locus) than the other, the individual reference result has two alleles and the individual reference result is a match for the individual test result in respect of the higher allele of the individual test result, but not the lower allele, then the probability function may involve, with respect to the alleles of the individual reference result, one or more of:—a probability term for the matching allele that drop out did not occur; a probability term for the non-matching allele that drop out did occur; a probability term for stutter of the matching allele that stutter did occur; a probability term for one or both alleles of the individual test sample that a spurious allele occurs (preferably with a term relating to the frequency of occurrence of that allele in a population); a probability term for one or both alleles of the individual test sample that an artifact occurs.

Where the individual test result has two alleles, one being one repeat unit less (4 bases less for a tetrameric locus) than the other, the individual reference result has two alleles and the individual reference result is a match for the individual test result in respect of the lower allele, but not the higher allele, then the probability function may involve, with respect to the alleles of the individual reference result, one or more of:—a probability term for the matching allele that drop out did not occur; a probability term for the non-matching allele that drop out did occur, a probability term for stutter of the matching allele that stutter did occur; a probability term for one or both alleles of the individual test sample that a spurious allele occurs (preferably with a term relating to the frequency of occurrence of that allele in a population); a probability term for one or both alleles of the individual test sample that an artifact occurs.

Where the individual test result has two alleles, the individual reference result has two alleles and the individual reference result is a match for the individual test result in respect of the lower allele of the individual test result, but not the higher allele, then the probability function may involve, with respect to the alleles of the individual reference result, one or more of:—where the non-matching allele is one repeat unit more (or 4 bases more for a tetrameric locus) than the higher allele of the individual test result: a probability term for the matching allele that drop out did not occur; a probability term for the non-matching allele that drop out did occur; a probability term for stutter of the non-matching allele that stutter did occur; a probability term for one or both alleles of the individual test sample that a spurious allele occurs (preferably with a term relating to the frequency of occurrence of that allele in a population); a probability term for one or both alleles of the individual test sample that an artifact occurs: and where the non-matching allele is not one repeat unit more (or 4 bases more for a tetrameric locus) than the higher allele of the individual test result one or more of: a probability term for the matching allele that drop out did not occur; a probability term for the non-matching allele that drop out did occur; a probability term for stutter of the non-matching allele that stutter did not occur; a probability term for one or both alleles of the individual test sample that a spurious allele occurs (preferably with a term relating to the frequency of occurrence of that allele in a population); a probability term for one or both alleles of the individual test sample that an artifact occurs.

Where the individual test result has two alleles, the individual reference result has two alleles and the individual reference result is not a match for the individual test result in respect of the lower or higher allele of the individual test result, then the probability function may involve, with respect to the alleles of the individual reference result, one or more of:—where one of the non-matching allele is one repeat unit more (or 4 bases more for a tetrameric locus) than the higher allele of the individual test result: a probability term for both the non-matching alleles that drop out did not occur; a probability term for stutter of one of the non-matching alleles that stutter did occur; a probability term for one or both alleles of the individual test sample that a spurious allele occurs (preferably with a term relating to the frequency of occurrence of that allele in a population); a probability term for one or both alleles of the individual test sample that an artifact occurs: and where neither the non-matching alleles is one repeat unit more (or 4 bases more for a tetrameric locus) than the higher allele of the individual test result, one or more of: a probability term for both the non-matching alleles that drop out did occur; a probability term for stutter of the non-matching alleles that stutter did not occur; a probability term for one or both alleles of the individual test sample that a spurious allele occurs (preferably with a term relating to the frequency of occurrence of that allele in a population); a probability term for one or both alleles of the individual test sample that an artifact occurs.

Where the individual test result has two alleles, one being one repeat unit less (4 bases less for a tetrameric locus) than the other, the individual reference result has one allele and the individual reference result is a match for the individual test result in respect of the higher allele, then the probability function may involve, with respect to the alleles of the individual reference result, one or more of:—a probability term for the matching allele that drop out did not occur; a probability term for stutter of the matching allele that stutter did occur; a probability term for one or both alleles of the individual test sample that a spurious allele occurs (preferably with a term relating to the frequency of occurrence of that allele in a population); a probability term for one or both alleles of the individual test sample that an artifact occurs.

Where the individual test result has two alleles, one not being one repeat unit less (4 bases less for a tetrameric locus) than the other, the individual reference result has one allele and the individual reference result is a match for the individual test result in respect of the higher allele, then the probability function may involve, with respect to the alleles of the individual reference result, one or more of:—a probability term for the matching allele that drop out did not occur; a probability term for stutter of the matching allele that stutter did not occur; a probability term for one or both alleles of the individual test sample that a spurious allele occurs (preferably with a term relating to the frequency of occurrence of that allele in a population); a probability term for one or both alleles of the individual test sample that an artifact occurs.

Where the individual test result has two alleles, the individual reference result has one allele and the individual reference result is a match for the individual test result in respect of the lower allele, then the probability function may involve, with respect to the alleles of the individual reference result, one or more of:—a probability term for the matching allele that drop out did not occur; a probability term for stutter of the matching allele that stutter did not occur; a probability term for one or both alleles of the individual test sample that a spurious allele occurs (preferably with a term relating to the frequency of occurrence of that allele in a population); a probability term for one or both alleles of the individual test sample that an artifact occurs.

Where the individual test result has two alleles, the individual reference result has one allele and the individual reference result is not a match for the individual test result in respect of either allele, then the probability function may involve, with respect to the alleles of the individual reference result, one or more of:—where the non-matching allele is one repeat unit more (4 bases more for a tetrameric locus) than one of the individual test result alleles: a probability term for the non-matching allele that drop out did occur; a probability term for stutter of the non-matching allele that stutter did occur; a probability term for one or both alleles of the individual test sample that a spurious allele occurs (preferably with a term relating to the frequency of occurrence of that allele in a population); a probability term for one or both alleles of the individual test sample that an artifact occurs: and where the non-matching allele is not one repeat unit more (4 bases more for a tetrameric locus) than one of the individual test result alleles one or more of: a probability term for the non-matching allele that drop out did occur; a probability term for stutter of the non-matching allele that stutter did not occur; a probability term for one or both alleles of the individual test sample that a spurious allele occurs (preferably with a term relating to the frequency of occurrence of that allele in a population); a probability term for one or both alleles of the individual test sample that an artifact occurs.

Where the individual test result has one allele, the individual reference result has two alleles and the lower allele of the individual reference result is a match for the individual test result, then the probability function may involve, with respect to the alleles of the individual reference result, one or more of:—where the higher allele of the individual reference result is one repeat unit more (4 bases more for a tetrameric locus) than the allele of the individual test result; a probability term for the matching allele that drop out did not occur, a probability for the non-matching allele that drop out did occur; a probability term for stutter of the non-matching allele that stutter did occur; a probability term for one or both alleles of the individual test sample that a spurious allele does not occur (preferably with a term relating to the frequency of occurrence of that allele in a population); a probability term for one or both alleles of the individual test sample that an artifact does not occur: and where the higher allele of the individual reference result is not one repeat unit more (4 bases more for a tetrameric locus) than the allele of the individual test result one or more of: a probability term for the matching allele that drop out did not occur; a probability for the non-matching allele that drop out did occur; a probability term for stutter of the non-matching allele that stutter did not occur; a probability term for one or both alleles of the individual test sample that a spurious allele does not occur (preferably with a term relating to the frequency of occurrence of that allele in a population); a probability term for one or both alleles of the individual test sample that an artifact does not occur.

Where the individual test result has one allele, the individual reference result has two alleles and neither of the individual reference results is a match for the individual test result, then the probability function may involve, with respect to the alleles of the individual reference result, one or more of:—where one of the individual reference result is one repeat unit more (4 bases more for a tetrameric locus) than the allele of the individual test result: a probability term for one or both the non-matching alleles that drop out did occur; a probability for stutter of the non-matching allele which is one repeat unit more (4 bases more for a tetrameric locus) than the individual test result that stutter did occur; a probability term for one or both alleles of the individual test sample that a spurious allele does occur (preferably with a term relating to the frequency of occurrence of that allele in a population); a probability term for one or both alleles of the individual test sample that an artifact does occur: and where neither of the alleles of the individual reference result is one repeat unit more (4 bases more for a tetrameric locus) than the allele of the individual test result one or more of: a probability term for both the non-matching alleles that drop out did occur; a probability term for stutter of the non-matching allele that stutter did not occur; a probability term for one or both alleles of the individual test sample that a spurious allele does occur (preferably with a term relating to the frequency of occurrence of that allele in a population); a probability term for one or both alleles of the individual test sample that an artifact does occur.

Where the individual test result has one allele, the individual reference result has one allele and the alleles match then the probability function may involve, with respect to the alleles of the individual reference result, one or more of:—a probability term for the matching allele that drop out did not occur; a probability term for stutter for the matching allele that stutter does not occur; a probability term for the allele of the individual test sample that a spurious allele does not occur (preferably with a term relating to the frequency of occurrence of that allele in a population); a probability term for the allele of the individual test sample that an artifact does not occur.

Where the individual test result has one allele, the individual reference result has one allele and the alleles do no match then the probability function may involve, with respect to the alleles of the individual reference result, one or more of:—where the non-matching allele of the individual reference result is one repeat unit more (4 bases more for a tetrameric locus) than the allele of the individual test result; a probability term for the non-matching allele that drop out occurs; a probability term for stutter of the non-matching allele that stutter occurs; a probability term for the allele of the individual test sample that a spurious allele occurs (preferably with a term relating to the frequency of occurrence of that allele in a population); a probability term for the allele of the individual test sample that an artifact does occur.

The various possible routes for the individual stored result giving the individual sample result may include contamination giving one or more alleles in the individual sample result not present in the individual stored result.

The various possible routes for the individual stored result giving the individual sample result may include stutter giving one or more alleles in the individual sample result not present in the individual stored result.

The various possible routes for the individual stored result giving the individual sample result may include amplification of artifacts giving one or more alleles in the individual sample result not present in the individual stored result.

The various possible routes for the individual stored result giving the individual sample result may include allele drop out giving one or more alleles missing in the individual sample result present in the individual stored result.

The probability function may include a probability that contamination may occur. The probability that contamination may occur may be determined by one or more control determinations. The control determinations may be made in parallel with the determination of the identity of the alleles of the test sample. The control determinations may be made separately, for instance as a reference investigation used subsequently in two or more test sample determinations. The probability that contamination may occur may be provided for by theoretical predictions.

The probability function may include a probability that stutter may occur. The probability that stutter may occur may be determined by one or more control determinations. The control determinations may be made in parallel with the determination of the identity of the alleles of the test sample. The control determinations may be made separately, for instance as a reference investigation used subsequently in two or more test sample determinations. The probability that stutter may occur may be provided for by theoretical predictions.

The probability function may include a probability that allele dropout may occur. The probability that allele dropout may occur may be determined by one or more control determinations. The control determinations may be made in parallel with the determination of the identity of the alleles of the test sample. The control determinations may be made separately, for instance as a reference investigation used subsequently in two or more test sample determinations. The probability that allele dropout may occur may be provided for by theoretical predictions.

The probability function may include a probability that artifact reporting may occur. The probability that artifact reporting may occur may be determined by one or more control determinations. The control determinations may be made in parallel with the determination of the identity of the alleles of the test sample. The control determinations may be made separately, for instance as a reference investigation used subsequently in two or more test sample determinations. The probability that artifact reporting may occur may be provided for by theoretical predictions.

The spurious information may be due to contamination effects, allele dropout effects, locus dropout effects, stutter effects, artifact effects or other causes.

The contribution of the spurious information may lead to an allele being present which is not part of the DNA test sample, the absence of alleles which should be present from the DNA test sample, the presence of apparent alleles in positions one repeat unit (4 bases lower for a tetrameric locus) than the alleles in the DNA test sample.

Preferably the consideration is applied to a plurality of loci, ideally all loci for which individual stored results and/or individual test results exist.

The combination of probabilities produced by the respective considerations is preferably obtained by multiplying the probabilities together.

Two or more different determinations of the identities of the alleles in the test sample may be performed. The method may be applied to each set of individual test results thereby obtained. The expression of a likelihood ratio for respective sets of individual test results may be considered against one another and/or combined.

The expression of a likelihood ratio and/or a combined expression of a likelihood ratio that a given reference sample and test sample match may be generated for a plurality, ideally all, of the reference samples available. The reference samples may be ranked in order of the likelihood ratios of a match with the test sample, ideally descending order.

According to a second aspect of the invention we provide a method of indicating a likelihood ratio that evaluates that at least a part of a DNA test sample arose from a known source, the method involving:— one or more determinations of the identity of the alleles present at a locus for the DNA in the test sample, each determination defining an individual test result;

the determination of at least some of the theoretical allele identities which could have produced a given individual test result, these identities forming the individual reference results;

the determination of the identity of the alleles present at the locus for the DNA from the known source;

one of the theoretical allele identities being the identity determined for that locus for the known source;

the provision of a probability function for each individual reference result considered which is representative of at least some of the various possible routes by which that given individual reference result may lead to the given individual test result, that probability function further being representative of the likelihood of that individual reference result's occurrence and the possible routes to the individual test result which includes routes where spurious information contributes, this probability function forming defining the theoretical probability functions;

the theoretical probability functions for different individual reference results being combined to give an indication of the various ways in which the given individual test result could be reached, this combination forming the combined theoretical probability function;

the provision of a probability function for the individual reference result matching the known source's identity, which is representative of the manner in which that individual reference result leads to the individual test result, this forming the known source's theoretical function;

the known source's theoretical function and combined theoretical function being considered together to calculate the likelihood ratio.

The second aspect of the invention may include features, options or possibilities set out elsewhere in this document.

At least part of a DNA sample may refer to one source of a multi-source or mixed sample. The method may indicate calculation of a likelihood ratio relating to one or more sources of a defined nature, for instance the likelihood ratio may evaluate the proposition of two defined contributors to the sample.

The known source may refer to a known individual and/or be associated with one or more other known factors, such as a location, item or event the sample was recovered from.

The identity of the alleles at one or more of the loci of the test sample may be determined by short tandem repeat based investigation.

An individual sample result is preferably the allele or alleles detected for that given locus and/or the apparent alleles detected when that locus is considered. The individual sample result may comprise 0 to 50 alleles but more usually comprises 0 to 32 alleles.

The individual sample result may thus include the homozygous or heterozygous alleles of the test sample's source, homozygous and/or heterozygous alleles from DNA contamination of the test sample and/or stutters of these and/or other amplification artifacts.

The consideration is preferably provided for between 1 and 25 loci and more preferably between 1 and 16 loci. Preferably an equivalent consideration process is provided for each loci.

Whilst the technique is applicable to all loci, the loci for which allele identity is determined may particularly be selected to include one or more of HUMVWFA31, HUMTH01, D21S11, D18S51, HUMFIBRA, D8S1179, HUMAMGXA, HUMAMGY, D3S1358, HUMVWA, D16S539, D2S1338, Amelogenin, D8S1179, D21S11, D18S51, D19S433, HUMTH01, HUMFIBRA/FGA. The loci selected may particularly be each of D3S1358, HUMVWA, D16S539, D2S1338, Amelogenin, D8S1179, D21S11, D18S51, D19S433, HUMTH01, HUMFIBRA/FGA.

The theoretical identities may be determined from the alleles indicated in the individual test result. All possible theoretical identities may be determined, but more preferably those theoretical identities which could reasonably lead to the individual test result are determined. Those theoretical identities defined as reasonable may be all identities where an allele in the test sample is in common with the reference sample. The determination may involve providing theoretic identities corresponding to each permutation of two alleles, where at least one of those alleles matches an allele in the individual test result.

The provision of a theoretical probability function may involve the probability of getting that individual test result in any way, including through spurious information occurrence. Preferably the provision of a probability function may involve the probability of getting that individual test result in any way, including through spurious information occurrence, and the frequency of that given theoretical identity in a population. More preferably the provision of a probability function may involve the probability of getting that individual test result in any way, including through spurious information occurrence, and the frequency of that theoretical identity in a population, for each individual test result.

The theoretical probability function for each individual reference result theoretical identity is preferably defined in part by a probability for that individual reference results identity occurrence in a population. The theoretical probability function for each individual reference result is preferably defined in part by a probability for the various occurrences which would result in that individual reference result giving the individual test result.

Theoretical probability functions may be provided to account for each of the individual test results determined for a locus in the aforementioned manner. Preferably the theoretical probability functions for each individual test result given an individual reference result are combined, ideally before the theoretical probability function s for different individual reference results are combined. Preferably the theoretical probability functions for different individual test results are combined by multiplication. Preferably the theoretical probability functions for different individual reference results are combined by addition.

Where contamination is necessary to lead to the individual test result the probability preferably includes a probability term for spurious allele occurrence.

Where contamination must not occur to lead to the individual test result the probability preferably includes a probability term for spurious allele non-occurrence.

Where stutter is necessary to lead to the individual test result the probability preferably includes a probability term for stutter occurrence.

Where stutter must not occur to lead to the individual test result the probability preferably includes a probability term for stutter non-occurrence.

Where allele dropout is necessary to lead to the individual test result the probability preferably includes a probability term for allele dropout occurrence.

Where allele dropout must not occur to lead to the individual test result the probability preferably includes a probability term for allele dropout non-occurrence.

Where artifact reporting is necessary to lead to the individual test result the probability preferably includes a probability term for artifact reporting occurrence.

Where artifact reporting must not occur to lead to the individual test result the probability preferably includes a probability term for artifact reporting non-occurrence.

In the following definitions of probability functions, the probability function may include, and ideally is a multiple of, the probability of that possible identity occurring in a population.

Reference to a population may include the world population, a representative sample there of, an arbitrary selected population, pseudo-random population, database content or other population.

Where the individual test result has two alleles, the individual reference result has two alleles and the individual reference result is a match for the individual test result in respect of both alleles, then the probability function may involve, with respect to the alleles of the individual reference result, one or more of:—a probability term for one or both alleles that drop out did not occur; a probability term for one or both alleles that stutter did not occur; a probability term for one or both alleles that spurious alleles did not occur, a probability term for one or both alleles that other artifacts did not occur.

Where the individual test result has two alleles, one being one repeat unit less (or 4 bases less for a tetrameric locus) than the other, the individual reference result has two alleles and the individual reference result is a match for the individual test result in respect of the higher allele of the individual test result, but not the lower allele, then the probability function may involve, with respect to the alleles of the individual reference result, one or more of:—a probability term for the matching allele that drop out did not occur; a probability term for the non-matching allele that drop out did occur; a probability term for stutter of the matching allele that stutter did occur; a probability term for one or both alleles of the individual test sample that a spurious allele occurs (preferably with a term relating to the frequency of occurrence of that allele in a population); a probability term for one or both alleles of the individual test sample that an artifact occurs.

Where the individual test result has two alleles, one being one repeat unit less (4 bases less for a tetrameric locus) than the other, the individual reference result has two alleles and the individual reference result is a match for the individual test result in respect of the lower allele, but not the higher allele, then the probability function may involve, with respect to the alleles of the individual reference result, one or more of:—a probability term for the matching allele that drop out did not occur; a probability term for the non-matching allele that drop out did occur; a probability term for stutter of the matching allele that stutter did occur; a probability term for one or both alleles of the individual test sample that a spurious allele occurs (preferably with a term relating to the frequency of occurrence of that allele in a population); a probability term for one or both alleles of the individual test sample that an artifact occurs.

Where the individual test result has two alleles, the individual reference result has two alleles and the individual reference result is a match for the individual test result in respect of the lower allele of the individual test result, but not the higher allele, then the probability function may involve, with respect to the alleles of the individual reference result, one or more of:—where the non-matching allele is one repeat unit more (or 4 bases more for a tetrameric locus) than the higher allele of the individual test result, a probability term for the matching allele that drop out did not occur; a probability term for the non-matching allele that drop out did occur; a probability term for stutter of the non-matching allele that stutter did occur; a probability term for one or both alleles of the individual test sample that a spurious allele occurs (preferably with a term relating to the frequency of occurrence of that allele in a population); a probability term for one or both alleles of the individual test sample that an artifact occurs: and where the non-matching allele is not one repeat unit more (or 4 bases more for a tetrameric locus) than the higher allele of the individual test result on or more of: a probability term for the matching allele that drop out did not occur; a probability term for the non-matching allele that drop out did occur; a probability term for stutter of the non-matching allele that stutter did not occur; a probability term for one or both alleles of the individual test sample that a spurious allele occurs (preferably with a term relating to the frequency of occurrence of that allele in a population); a probability term for one or both alleles of the individual test sample that an artifact occurs.

Where the individual test result has two alleles, the individual reference result has two alleles and the individual reference result is not a match for the individual test result in respect of the lower or higher allele of the individual test result, then the probability function may involve, with respect to the alleles of the individual reference result, one or more of:—where one of the non-matching allele is one repeat unit more (or 4 bases more for a tetrameric locus) than the higher allele of the individual test result, a probability term for both the non-matching alleles that drop out did not occur; a probability term for stutter of one of the non-matching alleles that stutter did occur; a probability term for one or both alleles of the individual test sample that a spurious allele occurs (preferably with a term relating to the frequency of occurrence of that allele in a population); a probability term for one or both alleles of the individual test sample that an artifact occurs; and where neither the non-matching alleles is one repeat unit more (or 4 bases more for a tetrameric locus) than the higher allele of the individual test result one or more of: a probability term for both the non-matching alleles that drop out did occur; a probability term for stutter of the non-matching alleles that stutter did not occur; a probability term for one or both alleles of the individual test sample that a spurious allele occurs (preferably with a term relating to the frequency of occurrence of that allele in a population); a probability term for one or both alleles of the individual test sample that an artifact occurs.

Where the individual test result has two alleles, one being one repeat unit less (4 bases less for a tetrameric locus) than the other, the individual reference result has one allele and the individual reference result is a match for the individual test result in respect of the higher allele, then the probability function may involve, with respect to the alleles of the individual reference result, one or more of:—a probability term for the matching allele that drop out did not occur; a probability term for stutter of the matching allele that stutter did occur; a probability term for one or both alleles of the individual test sample that a spurious allele occurs (preferably with a term relating to the frequency of occurrence of that allele in a population); a probability term for one or both alleles of the individual test sample that an artifact occurs.

Where the individual test result has two alleles, one not being one repeat unit less (4 bases less for a tetrameric locus) than the other, the individual reference result has one allele and the individual reference result is a match for the individual test result in respect of the higher allele, then the probability function may involve, with respect to the alleles of the individual reference result, one or more of:—a probability term for the matching allele that drop out did not occur; a probability term for stutter of the matching allele that stutter did not occur; a probability term for one or both alleles of the individual test sample that a spurious allele occurs (preferably with a term relating to the frequency of occurrence of that allele in a population); a probability term for one or both alleles of the individual test sample that an artifact occurs.

Where the individual test result has two alleles, the individual reference result has one allele and the individual reference result is a match for the individual test result in respect of the lower allele, then the probability function may involve, with respect to the alleles of the individual reference result, one or more of:—a probability term for the matching allele that drop out did not occur; a probability term for stutter of the matching allele that stutter did not occur; a probability term for one or both alleles of the individual test sample that a spurious allele occurs (preferably with a term relating to the frequency of occurrence of that allele in a population); a probability term for one or both alleles of the individual test sample that an artifact occurs.

Where the individual test result has two alleles, the individual reference result has one allele and the individual reference result is not a match for the individual test result in respect of either allele, then the probability function may involve, with respect to the alleles of the individual reference result, one or more of:—where the non-matching allele is one repeat unit more (4 bases more for a tetrameric locus) than one of the individual test result alleles, a probability term for the non-matching allele that drop out did occur; a probability term for stutter of the non-matching allele that stutter did occur; a probability term for one or both alleles of the individual test sample that a spurious allele occurs (preferably with a term relating to the frequency of occurrence of that allele in a population); a probability term for one or both alleles of the individual test sample that an artifact occurs: and where the non-matching allele is not one repeat unit more (4 bases more for a tetrameric locus) than one of the individual test result alleles, on or more of: a probability term for the non-matching allele that drop out did occur; a probability term for stutter of the non-matching allele that stutter did not occur; a probability term for one or both alleles of the individual test sample that a spurious allele occurs (preferably with a term relating to the frequency of occurrence of that allele in a population); a probability term for one or both alleles of the individual test sample that an artifact occurs.

Where the individual test result has one allele, the individual reference result has two alleles and the lower allele of the individual reference result is a match for the individual test result, then the probability function may involve, with respect to the alleles of the individual reference result, one or more of:—where the higher allele of the individual reference result is one repeat unit more (4 bases more for a tetrameric locus) than the allele of the individual test result: a probability term for the matching allele that drop out did not occur, a probability for the non-matching allele that drop out did occur; a probability term for stutter of the non-matching allele that stutter did occur; a probability term for one or both alleles of the individual test sample that a spurious allele does not occur (preferably with a term relating to the frequency of occurrence of that allele in a population); a probability term for one or both alleles of the individual test sample that an artifact does not occur: and where the higher allele of the individual reference result is not one repeat unit more (4 bases more for a tetrameric locus) than the allele of the individual test result, one or more of: a probability term for the matching allele that drop out did not occur; a probability for the non-matching allele that drop out did occur; a probability term for stutter of the non-matching allele that stutter did not occur; a probability term for one or both alleles of the individual test sample that a spurious allele does not occur (preferably with a term relating to the frequency of occurrence of that allele in a population); a probability term for one or both alleles of the individual test sample that an artifact does not occur.

Where the individual test result has one allele, the individual reference result has two alleles and neither of the individual reference results is a match for the individual test result, then the probability function may involve, with respect to the alleles of the individual reference result, one or more of:—where one of the individual reference result is one repeat unit more (4 bases more for a tetrameric locus) than the allele of the individual test result: a probability term for one or both the non-matching alleles that drop out did occur; a probability for stutter of the non-matching allele which is one repeat unit more (4 bases more for a tetrameric locus) than the individual test result that stutter did occur; a probability term for one or both alleles of the individual test sample that a spurious allele does occur (preferably with a term relating to the frequency of occurrence of that allele in a population); a probability term for one or both alleles of the individual test sample that an artifact does occur: and where neither of the alleles of the individual reference result is one repeat unit more (4 bases more for a tetrameric locus) than the allele of the individual test result, one or more of: a probability term for both the non-matching alleles that drop out did occur; a probability term for stutter of the non-matching allele that stutter did not occur; a probability term for one or both alleles of the individual test sample that a spurious allele does occur (preferably with a term relating to the frequency of occurrence of that allele in a population); a probability term for one or both alleles of the individual test sample that an artifact does occur.

Where the individual test result has one allele, the individual reference result has one allele and the alleles match then the probability function may involve, with respect to the alleles of the individual reference result, one or more of:—a probability term for the matching allele that drop out did not occur; a probability term for stutter for the matching allele that stutter does not occur; a probability term for the allele of the individual test sample that a spurious allele does not occur (preferably with a term relating to the frequency of occurrence of that allele in a population); a probability term for the allele of the individual test sample that an artifact does not occur.

Where the individual test result has one allele, the individual reference result has one allele and the alleles do no match then the probability function may involve, with respect to the alleles of the individual reference result, one or more of:—where the non-matching allele of the individual reference result is one repeat unit more (4 bases more for a tetrameric locus) than the allele of the individual test result: a probability term for the non-matching allele that drop out occurs; a probability term for stutter of the non-matching allele that stutter occurs; a probability term for the allele of the individual test sample that a spurious allele occurs (preferably with a term relating to the frequency of occurrence of that allele in a population); a probability term for the allele of the individual test sample that an artifact does occur.

The various possible routes for the individual reference result giving the individual test result may include contamination giving one or more alleles in the individual test result not present in the individual reference result.

The various possible routes for the individual reference result giving the individual test result may include stutter giving one or more alleles in the individual test result not present in the individual reference result.

The various possible routes for the individual reference result giving the individual test result may include amplification of artifacts giving one or more alleles in the individual test result not present in the individual reference result.

The various possible routes for the individual reference result giving the individual test result may include allele drop out giving one or more alleles missing in the individual test result present in the individual reference result.

The probability function may include a probability that contamination may occur. The probability that contamination may occur may be determined by one or more control determinations. The control determinations may be made in parallel with the determination of the identity of the alleles of the test sample. The control determinations may be made separately, for instance as a reference investigation used subsequently in two or more test sample determinations. The probability that contamination may occur may be provided for by theoretical predictions.

The probability function may include a probability that stutter may occur. The probability that stutter may occur may be determined by one or more control determinations. The control determinations may be made in parallel with the determination of the identity of the alleles of the test sample. The control determinations may be made separately, for instance as a reference investigation used subsequently in two or more test sample determinations. The probability that stutter may occur may be provided for by theoretical predictions.

The probability function may include a probability that allele dropout may occur. The probability that allele dropout may occur may be determined by one or more control determinations. The control determinations may be made in parallel with the determination of the identity of the alleles of the test sample. The control determinations may be made separately, for instance as a reference investigation used subsequently in two or more test sample determinations. The probability that allele dropout may occur may be provided for by theoretical predictions.

The probability function may include a probability that artifact reporting may occur. The probability that artifact reporting may occur may be determined by one or more control determinations. The control determinations may be made in parallel with the determination of the identity of the alleles of the test sample. The control determinations may be made separately, for instance as a reference investigation used subsequently in two or more test sample determinations. The probability that artifact reporting may occur may be provided for by theoretical predictions.

The spurious information may be due to contamination effects, allele dropout effects, locus dropout effects, stutter effects, artifact effects or other causes.

The contribution of the spurious information may lead to an allele being present which is not part of the DNA test sample, the absence of alleles which should be present from the DNA test sample, the presence of apparent alleles in positions one repeat unit less (or 4 bases less for a tetrameric locus) than the alleles in the DNA test sample.

The theoretical probability functions may be combined to give the overall combined theoretical probability function by summing the theoretical probability functions together.

The provision of the probability function results matching the known source's identity may involve the probability of getting that individual test result given that individual reference result, including through spurious information occurrence. Preferably the provision of the probability function for the individual reference may involve the probability of getting that individual test result given that individual reference result, including through spurious information occurrence, for each individual test result.

The known source's theoretical function and combined theoretical function may be combined as a ratio, preferably as a likelihood ratio. The likelihood ratio preferably accounts for the probability that a given individual reference result/theoretical identity leads to the individual test result against the probability that the individual test result was lead to in another way. The likelihood ratio may be the known source's theoretical function divided by the combined theoretical function.

Preferably the method is repeated for a plurality of loci, ideally all loci for which individual test results exist. The likelihood ratio obtained for each loci may be multiplied together to give a combined loci likelihood ratio.

Two or more different determinations of the identities of the alleles in the test sample may be performed. The method may be applied to each set of individual test results thereby obtained. The expression of the likelihood ratio for respective sets of individual test results may be considered against one another and/or combined.

According to a third aspect of the invention we provide a method of investigating the acceptable values for one or more variables relating to a DNA sample analysis, the method involving:— the consideration of one or more probability functions used in a method of indicating the likelihood ratio that at least part of a DNA sample arose from a known source, at least one of the probability functions being defined by an approximating function and a scaling factor, the scaling factor including at least one of the variables as a term;

the value for one or more of the variables in the scaling factor being assigned a plurality of different values and the value of the scaling factor being considered at each of those different values;

the value or values for the one or more variables being deemed acceptable when the value of the scaling factor is within a predetermined or acceptable range.

The third aspect of the invention may include any of the features, options or possibilities set out elsewhere in this document, including the first and/or second aspects of the invention.

The DNA sample analysis is preferably a consideration of the likelihood ratio that a sample arose from one or more scenarios compared with the sample arising from the other possible scenarios.

The probability functions may be particularly provided according to the definitions of the first and/or second aspects of the invention. The probability functions preferably take into account the probability of spurious information potentially contributing to the results obtained upon analysis of the sample.

The approximating function may provide an indication of the probability within certain acceptable ranges for potential variables of the analysis process. The approximating function may be an accurate assumption of the probability within these acceptable ranges. The approximating function may be an inaccurate assumption of the probability outside these acceptable ranges.

The scaling factor may account for one or more variables in the analysis. The one or more variables may be sources of error. The one or more variables may be probabilities of spurious information contributing to the results of the analysis of the sample. The spurious information sources may be one or more of allele/locus dropout, stutter, contamination or artifact reporting.

The variable value is preferably between 0 and 1 inclusive. The variable value may be assigned values at increments of 0.1 or less for the investigation. Preferably each combination of the incremental values is considered for the variables which contribute to a given scaling factor. A scaling factor may involve one, two, three, four or more variables depending upon the scaling factor. Preferably values for the scaling factor are determined for all possible combinations of the variable's values.

The acceptable range is preferably a range in which the scaling factor has a minimal effect on the probability function if it is included compared with if it is excluded. The range for the scaling factor may be between 0.9 and 1.1 in some cases. In other cases the scaling factor may be between 0.9 and 1.

According to a fourth aspect of the invention we provide a method of indicating a likelihood ratio that at least a part of a DNA sample arose from a known source or sources, the method involving:— the determination of the identity of the alleles present at a locus for the DNA in the sample, the determination defining an individual test result;

the determination of the identity of the alleles present at the locus for the known source; the consideration of a likelihood ratio that the known source leads to the individual test result compared with the other possible routes to the individual test result, the likelihood ratio being based on one or more probability functions, at least one of the probability functions being defined by an approximating function and a scaling factor, the scaling factor including at least one variable term relating to the probability of spurious information potentially contributing to the individual result;

the value of one or more of the variables being determined for the method;

the determined value of the one or more variables being considered against an acceptable range for that variable and/or the value of one or more of the scaling factors being considered against its acceptable range given that determined value for that variable, one or more of the probability functions defined by a scaling factor including that variable being deemed defined by the approximating function where that variable has a value within its acceptable range and/or where the scaling factor has a value within its predetermined or acceptable range, the so defined one or more probability functions being used as the basis for the likelihood ratio.

The fourth aspect of the invention may include any of the features, options or possibilities set out elsewhere in this document, including the first and/or second and/or third aspects of the invention.

The value of one or more of the variables may be determined for the method in a different way from the determination of one or more other variables. The determination may be carried out for the laboratory where the analysis of the DNA sample will be performed. The determination may be performed alongside the analysis. The determination may be performed separately form the analysis, including periodic determinations and even one off determinations. The determination may be made using control analyses, including negative and/or positive controls. Experimental deterioration is preferred for the contamination value, for instance. The determination may be made theoretically.

The acceptable range is preferably a range in which the scaling factor has a minimal effect on the probability function if it is included compared with if it is excluded. The range for the scaling factor may be between 0.9 and 1.1 in some cases. In other cases the scaling factor may be between 0.9 and 1.

The probability functions may be defined by the approximating function and scaling factor where the variable values for that probability function and/or the scaling factor value for that probability function is outside the acceptable ranges. One or more probability functions defined by the approximating function and scaling factor may be used in combination with one or more probability functions defined by the approximating function, but in general all the probability functions will be defined by either the approximating function and scaling factor or by the approximating factor alone.

BRIEF DESCRIPTION OF THE DRAWINGS

The invention will now be described, by way of example only, and with reference to the accompanying drawings in which:

FIG. 3 provides Table 1 which illustrates the calculation of the components of the likelihood ratio for an example where three individual results show evidence of spurious bands and allele dropout;

FIG. 4 illustrates Table 2 and the calculation of the components of the likelihood ratio for an example involving stutter;

FIG. 5 illustrates graphically the testing of the robustness of the F designation from example 1a;

FIG. 7a illustrates graphically the evaluation of the scaling function from example 2a;

FIG. 9 illustrates graphically the evaluation of the scaling function from example 3a; and FIG. 10 represents Table 3, an analysis of p(D) parameters derived from experimental observation.

Figure 1:
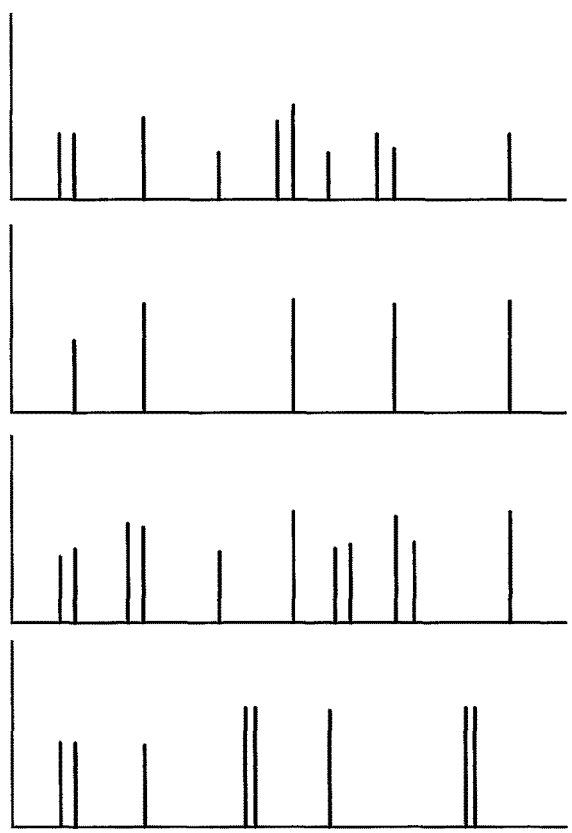
FIG. 1 illustrates the consideration of results from DNA analysis in a technique not according to the present invention.

In any DNA analysis technique the individual results can include information not arising from the DNA actually under investigation and/or not accurately represent the variations in the DNA in question which is actually being considered. This is particularly true for analysis techniques where amplification occurs, such as PCR based analysis. The problems become increasingly significant as the size of the initial DNA sample to be investigated becomes smaller. By the time investigations on a small number of cells are considered, 10 or less for instance, then substantial potential for such issues exists. In particular, even the lowest levels of DNA contamination from sample collection, laboratory handling or the equipment itself can have a marked effect on the individual results obtained. Additionally locus or allele dropout can occur and the amplified products may not fully reflect the DNA of the sample. There is also the possibility that stutters in the results will be in distinguishable from genuine allele results.

The outcome of these factors and others is that the potential for analysing small DNA samples is presently limited and where analysis is carried out it has to be handled by experts. Based on their knowledge and experience such expert individuals are able to consider the individual results and discard an individual result from further consideration where there is a question mark over it. This may lead to a substantial number of occasions where the individual result has to be discounted due to a negative control providing a response, with consequential cost and time implications. Additionally such processes are by their very nature subjective and equivalent sets of individual results may be handled by different experts in different ways. The discarding of many individuals from the initial set of results from further consideration also means that a high proportion of the individual results do not contribute in anyway to the overall findings.

The techniques of the present invention, whilst particularly useful in relation to consideration of small DNA samples, are useful in all DNA analysis techniques based around similar considerations.

The present invention in one embodiment below, aims to provide a system which takes in to account all the information obtained on a sample of unknown source and expresses a likelihood ratio that it matches with each of various known reference samples, rather than indicating a match or non-match against each. The present invention thus aims to reduce the skill required to perform an analysis but improve the accuracy and/or level of information provided by the analysis.

The present invention in one embodiment below, aims to provide a system which accounts for the other sources of information effectively and in a standardised way. The present invention, as embodied below, aims to provide results which are based on all of the initial individual results obtained, rather than the results after a screening process. In another embodiment, described below, the present invention aims to investigate and determine the impact of the other sources of information and particularly their probability of occurrence on a process for investigating DNA samples.

In another embodiment of the present invention, described below, the invention aims to provide a system which provides results for a DNA analysis technique based on certain approximations as to how the results are calculated, but with the validity of those approximations being checked.

The invention, as embodied below, aims to provide an effective process which does not require human expertise to interpret.

Sources of Spurious Information

To understand the operation of the invention it is useful to understand the nature of some of the possible error and other information sources which might be accounted for using the present invention. The predominant forms which can be accounted for are contamination with other DNA not originally in the sample; locus or allele drop out for information in the sample but not reporting in the results obtained; and stuttering where the amplified products include identities which are one repeat unit (or four bases less for a tetrameric locus) less than the associated allele and may be an allele too or a false amplification product.

Contamination of the DNA sample by DNA which was not originally part of the sample is a significant issue when small DNA samples are being amplified. Laboratory induced contamination is likely to occur on occasions as equipment and handling is not totally clean. Contamination results from fragments of cells in such amplification processes would be sufficient to give spurious results. Merely discarding an individual test when the negative control produces a result is not a viable option for small DNA sample analysis as a proportion of tests might give such a negative control result.

Locus/allele drop out is also a potential problem particularly with amplification of small DNA samples. A heterozygote sample should produce two alleles of the locus upon amplification. However, because amplification is an essentially random process, the fact that the amplification starts from only a few molecules may mean that problems with amplifying one of those alleles at an early stage lead to it not being present to a detectable degree in the amplification product. This can imply a homozygote identity where in reality the identity is heterozygote.

Stutters are artifacts from short tandem repeat systems and generally represent results one repeat unit (or four bases less for a tetrameric locus) than the associated allele.

Whilst stutters are predictable when large samples are amplified (they generally form a 15% peak compared with the associated allele peak). This is not the case in small sample amplification. As a consequence, stutters can appear close to and even exceed the size of the actual allele peaks. This can be a significant issue, particularly if the sample might be heterozygote with one of the alleles being four bases less than the other, and could consequently be confused with homozygote and stutter result.

Expressing a Likelihood of Match Between Test Sample and Reference Samples

In present analysis systems the result of the expert analysis is either that an individual result for the unknown sample is discounted from further consideration or is included in the results for further consideration. Thus the raw individual results, set A may be whittled down by the expert, excluding individual results which are caused for question, to give the individual results included for further consideration, set B in FIG. 1. This screened set, set B, is then compared with stored results for various samples of known origin, as exemplified by sets C and D in FIG. 1. A match is either agreed between the alleles forming the individual results, as between set B and set C in FIG. 1, or a match is not agreed, as between set B and set D in FIG. 1. Thus only some of the initial individual results are carried forward and the overall result is a match or not. The extent of the question marks over the raw individual results may lead to a substantial number being inconclusive and hence the match/non-match decision may be made based on a few points only and hence be of reduced statistical significance.

Figure 2:
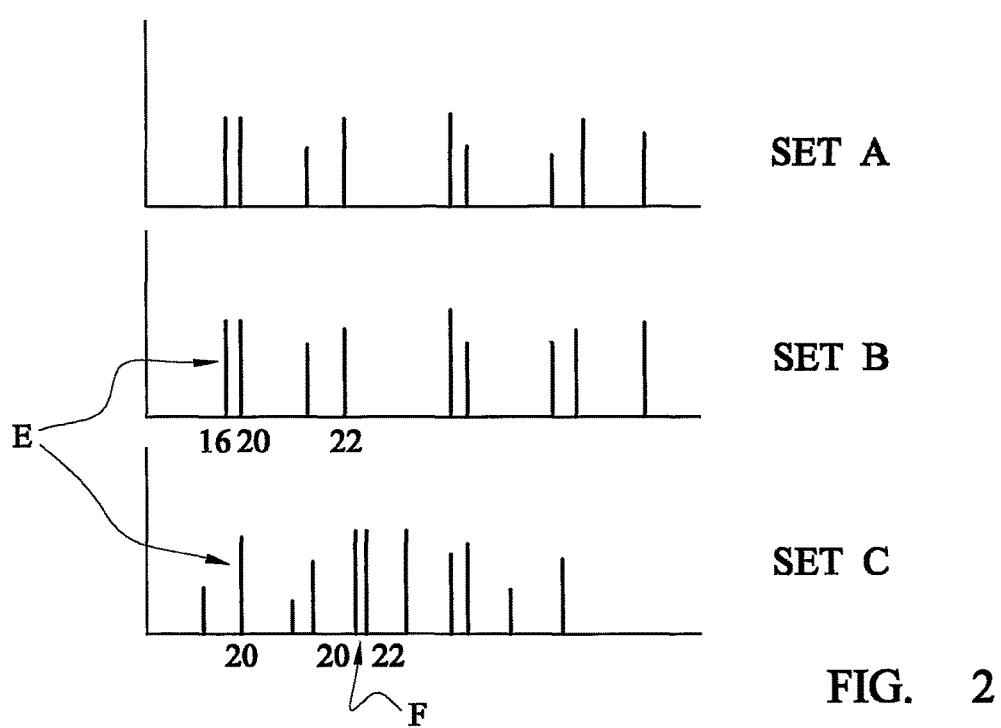
FIG. 2 illustrates the consideration of results from DNA analysis in a technique according to one embodiment of the present invention.

The technique in this embodiment of the present invention uses a very different approach. Once again, FIG. 2, the raw results are generated by the analysis process, set A. No screening process is carried out, however, and hence no expert input is required. Instead all the results are carried forward into set B which is used for comparison purposes with the stored results.

For explanatory purposes only a single stored result is considered for comparison, but in reality many such stored results would be considered in an equivalent manner. In basic terms the chance that each individual result in the test sample could have arisen given the stored sample result for the same locus and the various possibilities by which differences between the two could have arisen are considered. Thus, in the case of result E from set B alleles 16, 20 are observed and a direct match with the stored sample does not occur as that has allele 20 only. However, the technique considers the possibility that the 16 could have occurred due to contamination of the test sample with DNA have allele 16 and/or the possibility that the 16 could be a stutter for the 20 allele present in the DNA.

In a similar vein for result F from set B, allele 22 only, no match occurs as the stored sample has alleles 20 and 22. Rather than declaring a non-match, however, the technique considers the possibility that the 20 allele was not reported due to allele drop out during amplification.

In general it is preferred that the result be reported in terms of a likelihood ratio, based on the format, likelihood ratio, LR, is given by:—

$$LR = \frac{\text{Probability of the test sample result if it has the same origin as the stored sample}}{\text{Probability of the test sample result if it does not have the same origin as the stored sample}}$$

By pursuing such an approach for each of the individual results of the test sample against the individual results of the stored sample an overall likelihood that the test sample is a match for that particular stored sample can be obtained. Whilst the LR considers the likelihood against any way the test sample result could be reached, this may be restricted in practice to reasonable ways to simplify the calculations, but without loss of accuracy as the other ways are statistically very unlikely. From such overall likelihood ratios for a large number of stored samples lists can be obtained of descending likelihood ratios to be made between the stored samples and the test sample. Such a listing is more informative than a match or non-match statement, is less subjective as it does not involve an initial subjective screening process and is potentially more statistically significant as a greater number of individual results are considered.

The above mentioned technique means that all individual results are included for consideration; there is no need to exclude feared contamination results, stutter results or other artifact results from consideration. These events can be fully accounted for in the statistical consideration of the matter. There is also no need to worry that allele drop out will lead to an inconclusive or a non-match conclusive as the possibility of this occurring can be built in to the consideration.

Whilst the above mentioned considerations are particularly significant in small sample DNA analysis they are potential issues in all such analyses and benefits from the use of the technique thus apply in all levels of DNA consideration. The advantages in terms of removing subjective decisions also apply whatever the amount of starting DNA.

This type of technique can significantly simplify the interpretation of mixed DNA samples. Such situations occur, for instance, where a suspect may or may not have contributed to the mixture along with another known person and/or another unknown person as against the sample arising from an unknown person and another known person and/or unknown person. As against the previous methodology where interpretation was often impossible, the present invention always allows a likelihood ratio to be presented. Thus a likelihood ratio may be expressed as:—

$$LR = \frac{\text{Probability of the evidence if it comes from the stored sample and an unknown sample}}{\text{Probability of the evidence if it comes from two unknown samples}}$$

In such a case the analysis can consider each stored sample in the database in turn in making such an analysis.

Performing such considerations in an automated manner allows rapid consideration of a large number of stored samples against a test sample and/or allows a variety of scenarios to be considered (mixture is from suspect A and suspect B; mixture is from suspect A and suspect C; mixture is from suspect A and an unknown; etc,) very rapidly. This improvement is achieved whilst reducing cost and de-skilling the procedure.

The manner in which the probability of stored individual results leading to test individual result is set out in more detail below, in a different situation, but for which the same general principles apply.

Accounting for all Results

The technique of the invention generally aims to provide a likelihood ratio, LR, for the event being considered. In many cases this may be the likelihood that a suspect was the source of the DNA being analysed compared to the likelihood that the DNA source was someone else.

Given the potential impact of the other information sources, one or more of these is taken into account using the technique of the present invention to provide a fuller appreciation of the circumstances which may have generated the DNA sample. In the first example discussed the potential impact of contamination and allele dropout are considered, but the technique is capable of application to other information sources and issues too.

Whatever the likelihood ratio analysis the initial results must be obtained. To achieve this the collected sample is subjected to an amplification process such as PCR, to make many multiple copies of the DNA present in the initial sample. Where the initial sample is formed of only a few cells the number of cycles used may be between 30 and 34 cycles to achieve the necessary number of copies. The amplification process is generally concerned with producing enough material for effective investigation of the allele identity at a large number of locations. Techniques for analysing mixtures are known based around the use of short tandem repeats (STR's) as described by Clayton et al (1998) Analysis and Interpretation of Mixed Forensic Stains Using DNA STR Profiling, Int. J. Forensic Sci. 91, 55-70.

EXAMPLE—CONTAMINATION AND ALLELE DROP OUT IMPACT

In general terms the likelihood ratio in such cases considers the product of:— the probability that a given individual result for a locus under test arose, given the suspect's identity (homozygote) or identities (heterozygote) for the locus, by the various possible routes, including the suspects potential contribution and the potential other information source contribution for each of the given individual results; as the numerator relative to the product of:— the probability that a given individual result for a locus under test arose given one of all the possible identity combinations for that locus, by the various possible routes, including potential other information source contributions for each of the given individual results and each of the possible identity combinations; and the probability of that identity combination occurring; as the denominator.

To exemplify this approach in more detail a sample calculation based on three different individual results being obtained for a given locus is considered against a suspects identity for that locus. The three individual results are:—

$R_1=12$
$R_2=16$
$R_3=12,16$ with the suspects identity being 12,16.

If $H_1$ is the probability of the evidence if the profile is the suspect's and $H_2$ is the probability of the evidence if the profile is of someone other than the suspect, then the process starts by considering all the reasonable identities which might have occurred for the alleles under question. It is possible to account for all the possible identities which might have occurred for the alleles, but many of these are so unlikely as to not need accounting for in practice. The first column of Table 1 (FIG. 3) accounts for the three likely identities in this case, 12,12; 12, 16; 16,16.

In the next stage the probability of that allele identity occurring is stated, column 2, giving $f_{12}^2$; $2f_{12}f_{16}$; $f_{16}^2$; respectively, the $2f_{12}f_{16}$ reflecting the fact that the identity could have been 12,16; or 16,12. This gives the relative balance between the various identities being the one to account for one or more of those allele identities being relatively rare, for instance.

In the next stage, column 3, the manner in which the first individual result, 12, could be reached given each of the three allele identities is evaluated. Thus if the allele identity where 12, 12, the way in which the individual result 12 occurred would be that there was no contamination of the sample and there was no allele drop out for the sample in that test. Thus the probability of this individual result arising with this identity is the probability that there is no allele drop out, designated $p(\overline{D})$ multiplied by the probability that there is no contamination or spurious results, designated $p(\overline{C})$. For this result with allele identity 12, 16 the probability is the probability of allele drop out (to account for 16 not reporting) multiplied by the probability of no allele drop out (to account for 12 reporting) multiplied by the probability of no spurious reports (to account for no spurious 16 arising). The equivalent process for result 12 with possible allele identity 16, 16 would be the product of the probability of allele dropout (to account for 16 not being reported), the probability of spurious reports (to account for 12 being reported) and the probability of 12 occurring as an allele (to account for differences in the likelihoods of that particular spurious allele occurring).

This process is repeated in columns 4 and 5 of Table 1 for the various individual results and possible identity combinations.

In practice the process would be repeated for a large number of individual results.

Column 6 of Table 1 represents the product of columns 2, 3, 4 and 5 and relates to the overall probability that the allele identity that row represents the set of actual individual results. The sum of column 6 gives the overall denominator for the likelihood ratio.

The numerator for the likelihood ratio is the product of columns 3, 4 and 5 for the row having the identity corresponding to the suspect's identity/alleles, in this case row 3. Overall this gives the formula:—

$$\frac{p(\overline{D})^4 p(\overline{C})^3 p(D)^2}{p(\overline{D})^2 p(\overline{C})p(D)p(C)^2 f_{12}^2 f_{16}^2 +}$$
$$2p(\overline{D})^4 p(\overline{C})^3 p(D)^2 f_{12} f_{16} +$$
$$p(\overline{D})^2 p(\overline{C})p(D)p(C)^2 f_{12}^2 f_{16}^6$$

But this can be reduced, by substitution with p(C), the probability that contamination has occurred, and $p(\overline{C})$, the probability that contamination has not occurred to:—

$$LR = \frac{1}{2f_{12}f_{16}\left[1 + \frac{f_{12}f_{16}p(C)^2}{p(D)p(\overline{D})^2 p(\overline{C})^2}\right]}$$

p(C) can be estimated from a history of observation and/or can be determined for a laboratory, for instance, by a series of negative control tests and a consideration of spurious bands arising in those.

p(D) can also be estimated from a history of observation and/or can be determined by experimentation.

EXAMPLE—EVALUATION OF STUTTER IMPACT

As a further example to the accounting for possible contamination and locus/allele drop out discussed above this example considers stutter impacts.

In the example calculation set out in Table 2 (FIG. 4) the position where the first individual result gives a,b,c and individual result two gives a,c is considered relative to a suspect who is ac and where b is a stutter position.

Thus in Table 2, column 1 gives the three reasonable possible identities which could have given the individual results and column 2 is the probability of those possible identities occurring.

The expressions in column 3 are derived as follows. Where the result is a,b,c and the identity being considered is a,b then the result could have occurred $p(C)^2$ where both a and b did not drop out (hence $p(\overline{D})^2$), where a spurious report occurs to provide c (hence $p(C)f_c$), and where no stutters for either a or b are reported (hence). In the next row the process generates $p(\overline{D})^2$ (as both a and c report); $p(\overline{St})$ (as there is no stutter for a); and the combination of $p(St) \cdot p(C)$ and $p(\overline{St}) \cdot p(C)f_b$ (to account for the b arising as a stutter rather than spurious and the b arising as a spurious not stutter respectively).

Again the products of columns 2, 3 and 4 for column 5 and the denominator in the likelihood ratio is the sum of column 5, the denominator being the product of columns 3 and 4 of row 3. This gives:—

$$\frac{p(\overline{D})^4 p(\overline{C})p(\overline{St})^3 [p(St)p(C) + p(\overline{St})p(C)f_b]}{2f_a f_b f_c^2 p(\overline{D})^3 p(D)p(C)^2 p(\overline{St})^4 +}$$
$$2f_a f_c p(\overline{D})^4 p(\overline{C})p(\overline{St})^3$$
$$[p(St)p(\overline{C}) + p(\overline{St})p(C)f_b] +$$
$$2f_a^2 f_b f_c p(\overline{D})^3 p(D)p(C)^2 p(\overline{St})^3$$

Again through substitution this can be reduced to:—

$$LR = \frac{1}{2f_a f_c \left[1 + \frac{p(C)^2 p(D) f_b (f_a + p(\overline{St}) f_c)}{p(\overline{C}) p(\overline{D}) \{p(St) p(\overline{C}) + p(\overline{St}) p(C) f_b\}}\right]}$$

The types of function used to achieve the likelihood ratio can of course combine consideration of contamination, locus/allele dropout and stutter effect in a single case. Other such potential sources of information, such as sub-population effects is also possible. This is desirable both because it is more consistent with the approaches employed in other areas of DNA interpretation but more importantly because it follows logically from the correct consideration of the conditional nature of the probability of a genotype of possible offenders GIVEN the suspect's genotype. All that is required is to replace $p(M_j)$ with the conditional probability $p(M_j|M_s)$.

Likelihood ratios calculated in this way take into account all of the individual results obtained by the analysis process.

Determining Impact of Variations in Probability of Other Information Sources Contributing As well as enabling the calculation of accurate likelihood ratios in DNA analysis, the equations also enable the impact of the likelihood that contamination occurs, dropout will occur or stutter will occur upon the analysis process to be considered. Such an investigation can be used to determine appropriate thresholds for those probabilities before which certain approximations can be deemed to be held true and beyond which certain approximations can be deemed to not hold true. This is, potentially pre-calculated information, could be stored and then used in a DNA analysis technique to determine whether the results obtained can be processed using an analysing process in which approximations for likelihood ratios or other presentation of the results are used. This concept is discussed in more detail below together with additional details of the particular approximations which might be used in particular circumstances or scenarios.

Using Approximations in Analysis and Results, with Check on Validity Conditions for the Approximation Whilst the initial embodiment of the invention sets out detailed calculation rates for likelihood ratios which take into account each and every one of the results fully, the functions used therein can be simplified in certain cases. For instance the formulae accounting for potential contamination and potential allele dropout:—

$$LR = \frac{1}{2f_{12} f_{16} \left[1 + \frac{f_{12} f_{16} p(C)^2}{p(D) p(\overline{D})^2 p(\overline{C})^2}\right]}$$

gives a scaling factor of 1 provided $p(C) < 0.3$ and hence the likelihood ratio approaches:—

$$LR \cup \frac{1}{2 f_{12} f_{16}}$$

Thus provided this threshold is not crossed the likelihood ratio can be validly calculated based on a substantial simplification.

Using this process a series of practical situations were considered and the impact of contamination and/or locus allele dropout and/or stutter were considered with a view to determining the appropriate approximations for such situations and the threshold considerations for the applicability of such approximations.

EXAMPLE 1A

Apparently Single Banded Profiles

When an apparent one-banded homozygotes is encountered in a crime stain ($R_1 = a$) and the peak area is small, this may mean that allele dropout has occurred i.e. the genotype may in fact be heterozygous. This is considered a possibility whenever the peak is close to background. At low peak area, our experimental observation confirms that the probability of allele dropout (p(D)) is high. If the allele in the crime stain is type a and the suspect is type ab then it would seem reasonable to limit $M_j$ to aa, ab or aF wherein F stands for any allele other than type a or type b. This gives, b the general process described above:—

$$LR = \frac{1}{2 f_a \left[1 + \frac{1 - 2p(D)}{2p(D)} f_a\right]}$$

Figure 5:
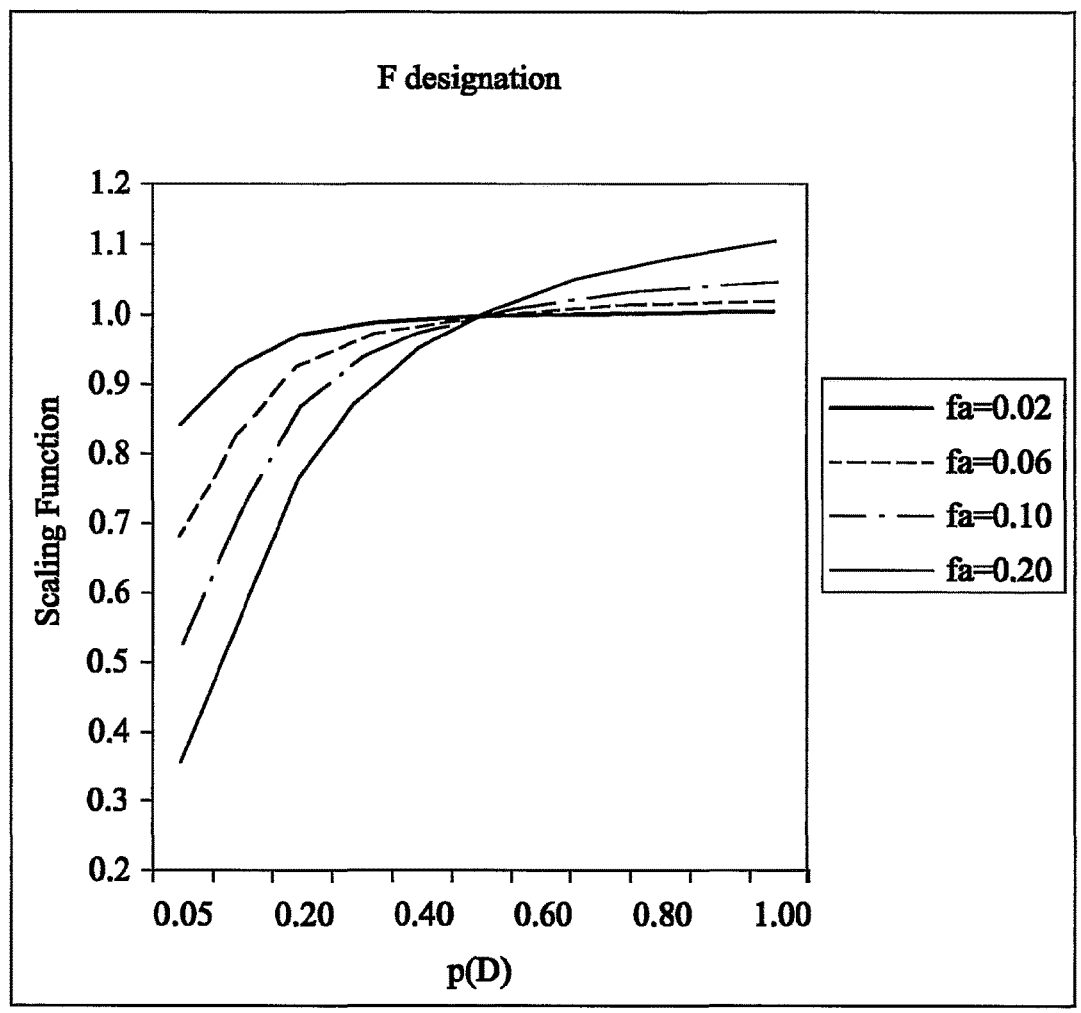

Provided that $p(D) > 0.5$, the scaling function $$\frac{1}{1 + \frac{1 - 2p(D)}{2p(D)} f_a} \geq 1.0$$

as illustrated in FIG. 5 which is always reasonable when the peak is close to the background, then the approximation is demonstrated to be conservative and $$LR \approx \frac{1}{2 f_a}$$

EXAMPLE 1B

Apparently One Banded Profiles—Effect of One Additional Replicate

Taking the previous example, we now consider the advantages of replication, where an additional aliquot ($R_2$) of the same DNA extract is separately amplified. Suppose that the second replicate yields a heterozygote ab that matches the suspect's profile (Suspect=ab; $R_1$=a−; $R_2$=ab).

We take account of three possible explanations of the evidence—either $M_1$=aa homozygote, else $M_2$=ab heterozygote. If the first explanation is true then the b allele must be a spurious band. In this example the LR would be reported as LR=½fa because only the a allele was duplicated. The formula that describes this model is:

$$LR = \frac{1}{2 f_a f_b \left[1 + \frac{f_a p(C)}{2 p(D) p(\overline{D}) p(\overline{C})}\right]}$$

This expression is always less than $\frac{1}{2} f_a f_b$ but the $\frac{1}{2} f_a$ evaluation is a conservative approximation whenever $$\frac{1}{f_b\left[1 + \frac{f_a p(C)}{2p(D)p(\overline{D})p(\overline{C})}\right]} \geq 1.0$$

and this is true for all reasonable estimates of p(C) and p(D).

If a locus appears homozygous with allele a, but allele drop-out could have occurred, so that the locus was really a heterozygote, then interpretation using $\frac{1}{2}f_a$ is reasonable provided that contamination is low and the allele peak area itself is small or close to the baseline.

EXAMPLE 1C

Additional Replicates Increase the LR

Continuing with the previous example, we consider the effect of additional (n) replicates that have been analysed and demonstrated to all correspond to the genotype of the suspect (ab in this example). The suspect is ab; $R_1$; $R_2$ ... $_n$=ab (i.e. a total of n+1 replicates were analysed). The general formula that describes $R_1$=a− and n=the number of replicates that the genotype ab is:

$$LR = \frac{1}{2f_a f_b\left[1 + \frac{f_a f_b^{n-1} p(C)^n}{2p(D)[p(\overline{D})p(\overline{C})]^n}\right]}$$

Figure 6A:
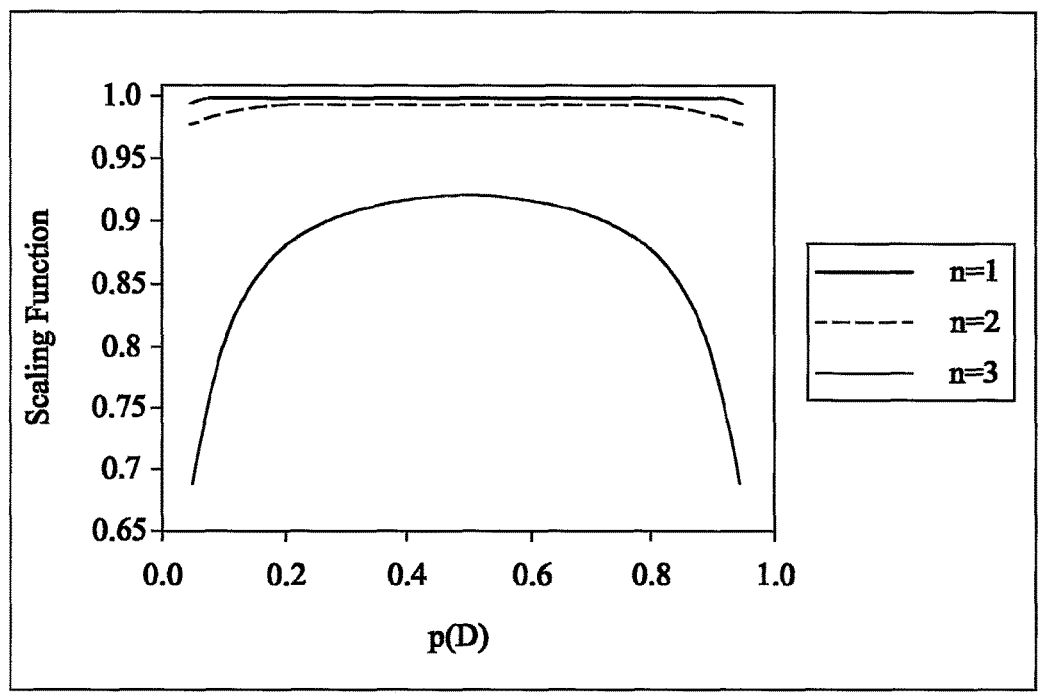
FIG. 6a illustrates graphically the evaluation of scaling factor in example 1c.
Figure 6B:
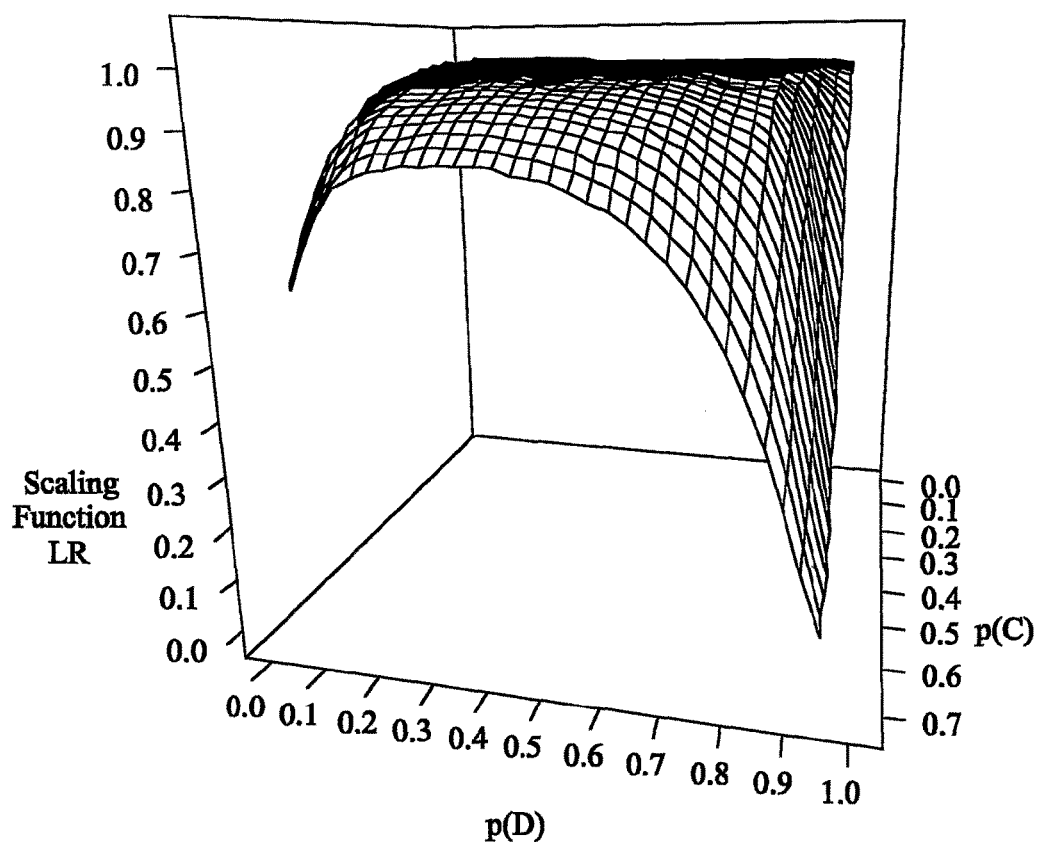
FIG. 6b illustrates graphically the evaluation of the scaling factor of example 1c three dimensionally.

Provided that n is greater than or equal to 2, the guideline will allow the reporting of LR=$\frac{1}{2}f_a f_b$ because both alleles are duplicated. The LR calculated from this equation will always be less than this but is nevertheless a very close approximate (see FIG. 6a) for most intermediate values of p(D). It is noted that the different between n=2 and n=3 is minor in these simulations. Also that the actual values of p(D) and p(C) have very little effect on the final estimate (see FIGS. 6a and 6b) provided that the latter is less than 0.6 (which it should always be). If n=1 then the LR is conservative relative to $\frac{1}{2}f_a$.

EXAMPLE 2A

An Example where an Allegedly Contaminant Band is Observed in Conjunction with Allele Dropout The next example is more extreme than those previously discussed. Suppose that a replicate ($R_1$) matches the suspect at one allele (b), but has an additional allele (c) that is not found in the suspect under the prosecution hypothesis ($H_1$). Furthermore, we assume that there is no trace of allele a. We assess the condition where the suspect is ab; $R_1$ is bc; $R_2$ is ab by consideration of the genotypes ($M_j$) ab, ac, bc and bb:

$$LR = \frac{1}{2f_a f_b\left[2 + \frac{f_b p(D) p(C)}{p(\overline{D})p(\overline{C})} + \frac{f_b p(C)}{2p(\overline{D})p(D)p(\overline{C})}\right]}$$

Figure 7A:
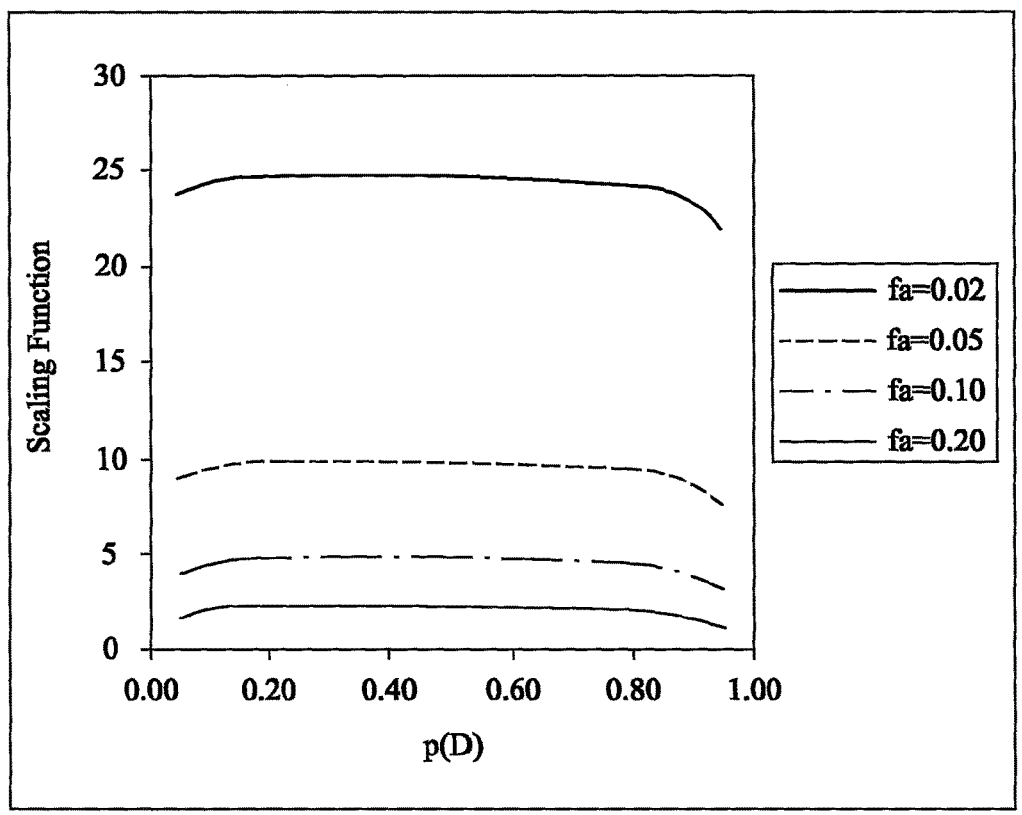
Figure 7B:
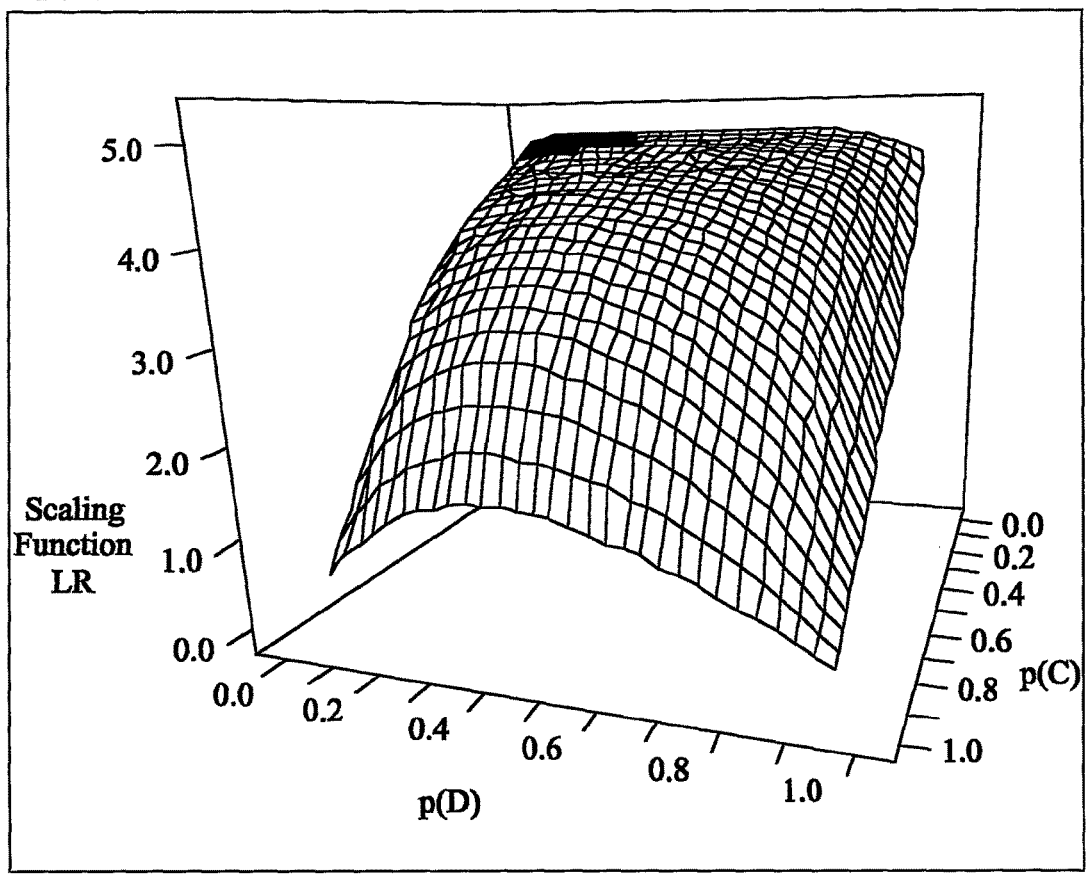
FIG. 7b illustrates graphically the evaluation of the scaling factor from example 2a three dimensionally.

The reporting guideline would only allow reporting of the duplicated b allele hence the reported likelihood ratio would be LR=$\frac{1}{2}f_b$. There was very little effect contributed by p(D) since the scaling function was always greater than 1.0 even when p(C) was moderately high (see FIG. 7a, 7b) demonstrating the conservative nature of the reporting guideline.

EXAMPLE 2B

Example where an Allegedly Contaminant Band is Observed

Figure 8A:
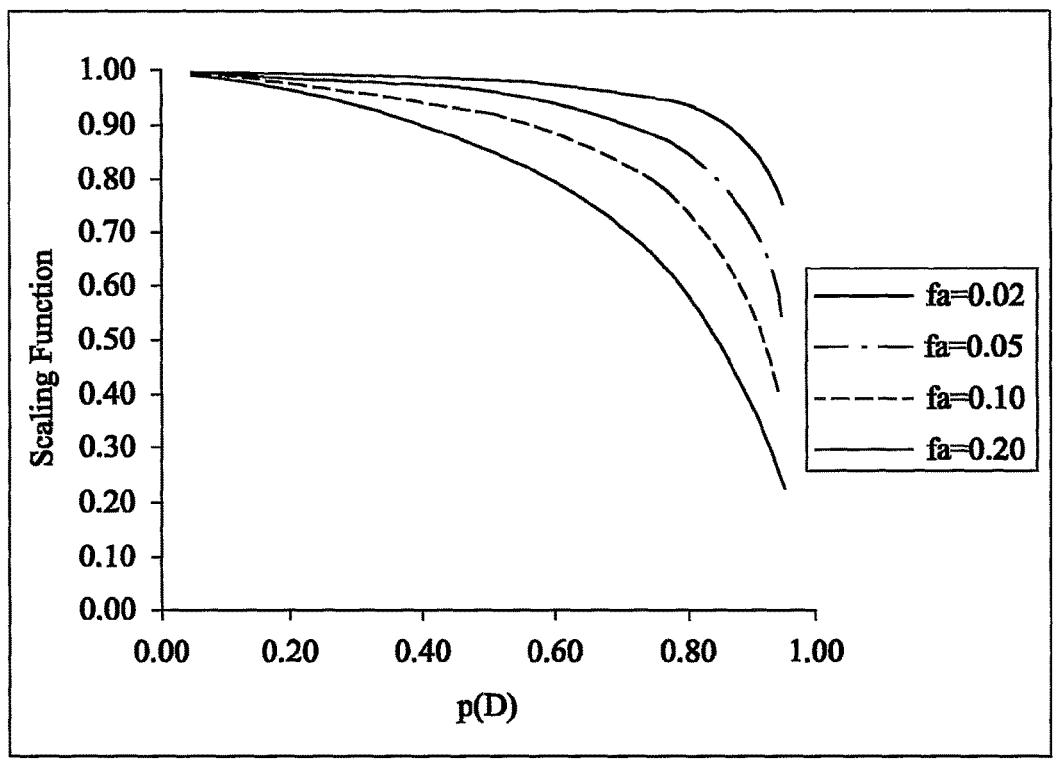
FIG. 8a illustrates graphically the evaluation of the scaling factor from example 2b.
Figure 8B:
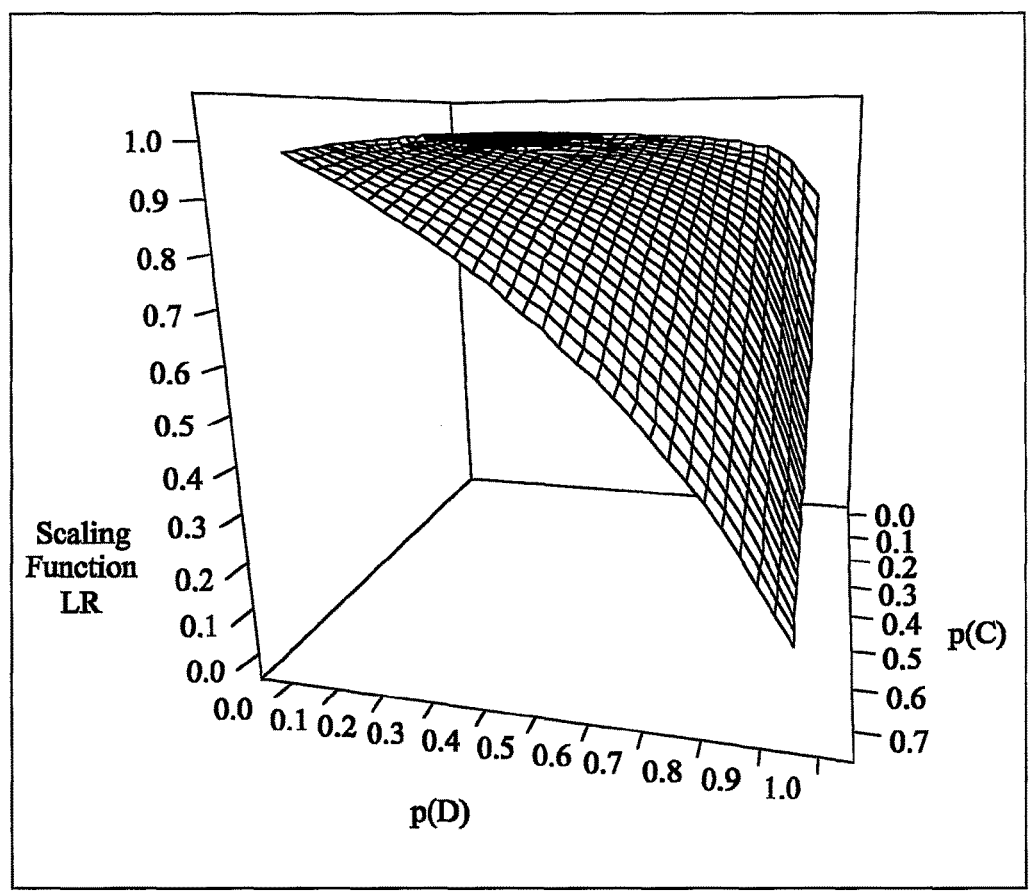
FIG. 8b illustrates graphically the evaluation of the scaling factor from example 2b three dimensionally.

Suppose that the suspect is ab; $R_1$=abc (where c is a supposedly a contaminant allele under $_1$) and $R_2$=ab. We limit the possible ($M_j$) genotypes to ab, ac or bc and we evaluate against the guideline LR≈$\frac{1}{2}f_a f_b$ (see FIGS. 8a, 8b). Evaluated against p(C)=0.3, the approximation is reasonable provided that $f_a$ is less than 0.10 and p(D) is less than 0.50.

$$\frac{1}{2f_a f_b\left[1 + p(D)p(C)\left(\frac{f_a + f_b}{p(\overline{D})p(\overline{C})}\right)\right]}$$

EXAMPLE 3A

In the case of the stutter counting for formula described above:—

$$LR = \frac{1}{2f_a f_c\left[1 + \frac{p(C)^2 p(D) f_b (f_a + p(\overline{St}) f_c)}{p(\overline{C})p(\overline{D})\{p(St)p(\overline{C}) + p(\overline{St})p(C)f_b\}}\right]}$$

Figure 9:
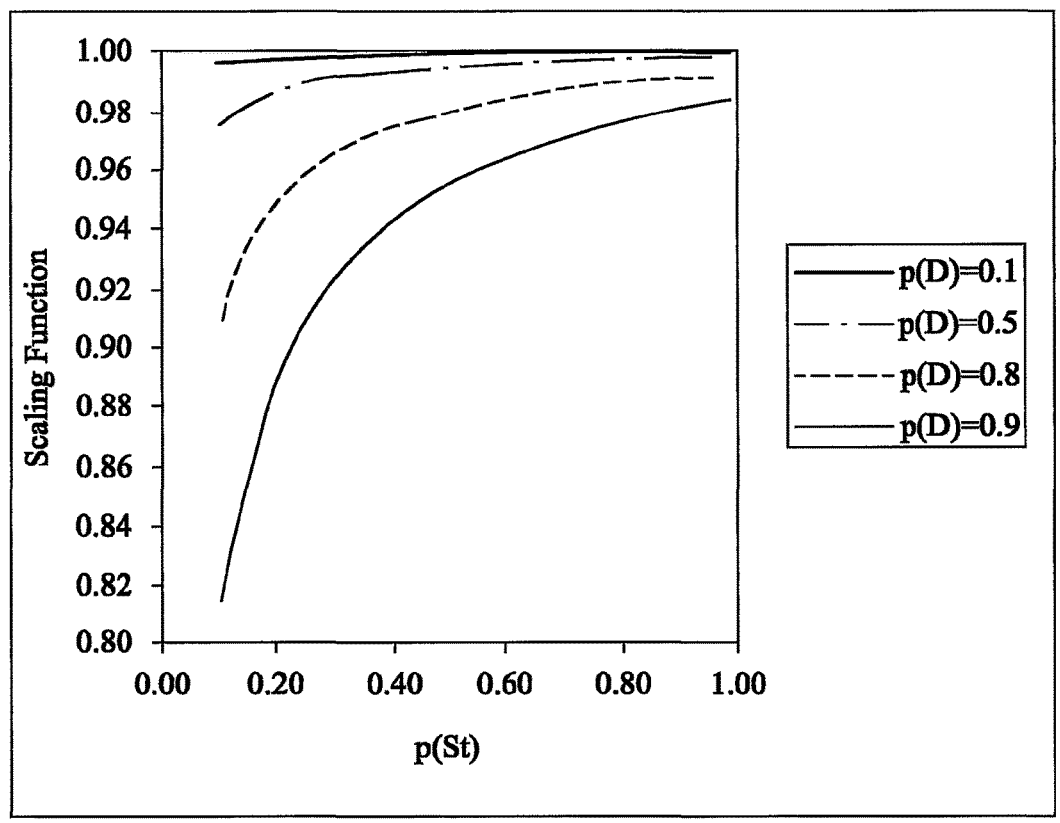

The scaling function is always less than 1, (as demonstrated by FIG. 9) and LR approximates to $\frac{1}{2}f_a f_c$. Investigation of this establishes that it is a good approximation provided p(St)>0.5 and p(C)<0.3.

EXAMPLE 3B

Extension of the Dropout Definition and Evaluation of an Actual Example

50PCR replicates of a sample that had 4 homozygous STRs and 6 heterozygous loci were analysed. We now expand the definition of p(D) as follows:

$p(D_{Ho})$—the probability of dropout given that the locus is homozygous.

$p(D_{He})$—the probability that a given allele drops out given that the locus is heterozygous.

$p(D_{He2})$—the probability that both alleles drop out given that the locus is heterozygous.

In the following calculations the p(D) parameters were either assigned the actual observed values in table 3 (FIG. 10) or if not available, e.g. ($pD_{He}$) for locus D8S51179, the mean across available loci was used instead. By observation, p(C) did not exceed 0.2 for any locus and this value was adopted throughout. Allele frequencies were used from a white Caucasian database.

From two of the replicates, we consider an extreme observation in table 5 for the locus D3S1358. The suspect is 18,18; $R_1$=15,18 and $R_2$=15,18. Conventional analysis may indicate the results to be either inconclusive or an exclusion since a spurious allele is duplicated in the replicates. Using the formula below, limiting our considerations of $M_j$ genotypes to 15,15; 15,18 and 18,18; the LR=0.068. The evidence supports exclusion, but importantly, the LR is greater than zero.

$$LR = \cfrac{1}{f_{18}{}^2 \left[ 2 + \cfrac{2\{p(\overline{D}_{He})\}^2 p(\overline{C})\}^2}{\{p(\overline{D}_{Ho})p(C)\}^2 f_{15} f_{18}} \right]}$$

At locus D8 the suspect is 15 15; R1=R2=15 F. The $M_j$ genotypes are limited to 15 15 and 15 F:

$$LR = \cfrac{1}{2f_{15}\left[ \cfrac{f_{15}}{2} + \cfrac{\{p(\overline{D}_{He})p(D_{He})\}^2(1-f_{15})}{p(\overline{D}_{Ho})^2} \right]}$$

In HUMTH01, $R_1$ was analysed as 7 F whereas $R_2$ failed to give a result. The suspect is 7 9.3. Our evaluation of the LR is limited to 7 F; 7 7 and 7 9.3 genotypes. However, the observation that 2 alleles have dropped out in $R_2$ is also built into the LR calculation below as shown in table 3.

$$LR = \cfrac{1}{2f_7\left[ 1 + \cfrac{p(\overline{D}_{Ho})p(D_{Ho})f_7}{2p(\overline{D}_{He})p(D_{He})p(D_{He2})} - f_7 \right]}$$

Similarly for VWA, $R_1$ failed to give a result and only one allele was observed in $R_2$. Our $M_j$ genotype considerations are limited to 19 19 and 19 F. The suspect is 19 19:

$$LR = \cfrac{1}{2f_{19}\left[ \cfrac{f_{19}}{2} + \cfrac{p(\overline{D}_{He})p(D_{He2})(1-f_{19})}{p(\overline{D}_{Ho})p(D_{Ho})} \right]}$$

For D16S539, $R_1$ is 9 12 and $"_2$ failed to give a result. We limit the evaluation of 9 9, 9 12 and 12 12 $M_j$ genotypes, considering the possibility of spurious alleles. The suspect is 9 12. Again we build the $R_2$ observation into the LR below:

$$LR = \cfrac{1}{2f_9 f_{12}\left[ 1 + \cfrac{p(\overline{D}_{Ho})p(D_{Ho})p(C)\{f_9 + f_{12}\}}{2p(\overline{D}_{He})^2 p(\overline{C})p(D_{He2})} \right]}$$

D18S51 is straight-forward since the 12 16 genotype was observe in both replicates. The analysis of D2S133 follows from the equation applied to HUMTH01 above.

Examination of the individual LRs calculated using these equations reveals that all are either conservative or very close to the estimates derived by calculating $LR=2f_a$ for homozygotes or $LR=2f_a f_b$ for the D16S539 heterozygote (table 3). When complete locus dropout is observed in a replicate this has very little effect, i.e. the scaling function ≈1.0. The combined LR across all loci=68,000 (using a white Caucasian database) and this serves to demonstrate that apparent allele mismatches caused by contamination do not necessarily lead to exclusions.

As is demonstrated by these various examples, therefore, the present invention generally provides a technique which can be used to evaluate the impact of variations in the probabilities of occurrence of various other information sources and extend that information to verification of the accuracy in applying certain assumptions to DNA analysis techniques.

The invention claimed is:

1. A computer-implemented method of comparing one or more reference samples of DNA from known individuals with a test sample of DNA, the method comprising:
   determining the identity of alleles present at a plurality of loci in the DNA of the test sample to give a plurality of respective individual test results;
   comparing each of the plurality of individual test results against a corresponding individual reference result of the one or more reference samples for the respective loci, the corresponding individual reference result comprising the identities of alleles present in the DNA of one of the reference samples at the same respective locus as the individual test result, the comparison involving an expression of the probability that the individual reference result for that locus could lead by various possible routes to the individual test result for the locus, the possible routes to the individual test result including routes where spurious information contributes to the individual test result, the expression of the probability is a probability function that includes more than one of a probability that contamination may occur, a probability that stutter may occur, a probability that allele dropout may occur, and a probability that artefact reporting may occur;
   when contamination is one of the types of spurious information considered and where contamination is necessary to lead from the individual reference result to the individual test result, the probability includes a probability term for spurious allele occurrence;
   when contamination is one of the types of spurious information considered and where contamination must not occur to lead from the individual reference result to the individual test result, the probability includes a probability term for spurious allele non-occurrence;
   when stutter is one of the types of spurious information considered and where stutter is necessary to lead from the individual reference result to the individual test result, the probability includes a probability term for stutter occurrence;
   when stutter is one of the types of spurious information considered and where stutter must not occur to lead from the individual reference result to the individual test result, the probability includes a probability term for stutter non-occurrence;
   when allele dropout is one of the types of spurious information considered and where allele dropout is necessary to lead from the individual reference result to the individual test result, the probability includes a probability term for allele dropout occurrence;
   when allele dropout is one of the types of spurious information considered and where allele dropout must not occur to lead from the individual reference result to the individual test result, the probability includes a probability term for allele dropout non-occurrence;
   when artifact reporting is one of the types of spurious information considered and where artifact reporting is necessary to lead from the individual reference result to the individual test result, the probability includes a probability term for artifact reporting occurrence;
   when artifact reporting is one of the types of spurious information considered and where artifact reporting must not occur to lead from the individual reference result to the individual test result, the probability includes a probability term for artifact reporting non-occurrence;

combining the expressions of probability that the individual reference result could lead to the individual test result for the plurality of loci to give a likelihood ratio of the probability that the test sample matches the reference sample; and, determining whether or not the DNA of the test sample originated from one or more of the known individuals based on the likelihood ratio.

2. A method according to claim 1 in which the test sample is from a known individual, a location, item or event that the sample was recovered from.

3. A method according to claim 1 in which the comparison involves the determination of a likelihood ratio, the likelihood ratio accounting for the probability of the individual test result arising from the individual reference result against the probability of the individual test result arising from other than the individual reference result.

4. A method according to claim 1 in which in order to evaluate a mixture for a known and unknown contributor scenario, the likelihood ratio is the probability of the individual test result arising from an individual reference result and other than the individual reference result divided by the probability of the individual test result arising from other than the individual reference result and from other than the individual stored result.

5. A method according to claim 1 in which the probability of observation of alleles is calculated from the frequency of occurrence in relevant populations and used in the consideration.

6. A method according to claim 1 in which the probability function includes a probability that contamination may occur, the probability that contamination may occur being determined by one or more control determinations.

7. A method according to claim 1 in which the probability function includes a probability that stutter may occur, the probability that stutter may occur being determined by one or more control determinations.

8. A method according to claim 1 in which the probability function includes a probability that allele dropout may occur, the probability that allele dropout may occur being determined by one or more control determinations.

9. A method according to claim 1 in which, the probability function includes a probability that artefact reporting may occur, the probability that artefact reporting may occur being determined by one or more control determinations.

10. A method according to claim 1 in which the comparison is applied to all loci for which individual reference results and individual test results exist.

11. A method according to claim 1 in which the combination of probabilities produced by the respective comparisons is obtained by multiplying the probabilities together.

12. A method according to claim 1 in which two or more different determinations of the identities of the alleles in the test sample are performed, the method being applied to each set of individual test results thereby obtained, the expression of a likelihood ratio for respective sets of individual test results being compared against one another and/or combined.

13. A method according to claim 1, wherein the method forms part of a forensic investigation in which the known individuals are suspects and the test sample is a crime stain.

14. A system configured to perform a computer-implemented method of comparing one or more reference samples of DNA from known individuals with a test sample of DNA, the method comprising:

determining the identity of alleles present at a plurality of loci in the DNA of the test sample to give a plurality of respective individual test results;

comparing each of the plurality of individual test results against a corresponding individual reference result of the one or more reference samples for the respective loci, the corresponding individual reference result comprising the identities of alleles present in the DNA of one of the reference samples at the same respective locus as the individual test result, the comparison involving an expression of the probability that the individual reference result for that locus could lead by various possible routes to the individual test result for the locus, the possible routes to the individual test result including routes where spurious information contributes to the individual test result, the expression of the probability is a probability function that includes more than one of a probability that contamination may occur, a probability that stutter may occur, a probability that allele dropout may occur, and a probability that artefact reporting may occur;

when contamination is one of the types of spurious information considered and where contamination is necessary to lead from the individual reference result to the individual test result, the probability includes a probability term for spurious allele occurrence;

when contamination is one of the types of spurious information considered and where contamination must not occur to lead from the individual reference result to the individual test result, the probability includes a probability term for spurious allele non-occurrence;

when stutter is one of the types of spurious information considered and where stutter is necessary to lead from the individual reference result to the individual test result, the probability includes a probability term for stutter occurrence;

when stutter is one of the types of spurious information considered and where stutter must not occur to lead from the individual reference result to the individual test result, the probability includes a probability term for stutter non-occurrence;

when allele dropout is one of the types of spurious information considered and where allele dropout is necessary to lead from the individual reference result to the individual test result, the probability includes a probability term for allele dropout occurrence;

when allele dropout is one of the types of spurious information considered and where allele dropout must not occur to lead from the individual reference result to the individual test result, the probability includes a probability term for allele dropout non-occurrence;

when artifact reporting is one of the types of spurious information considered and where artifact reporting is necessary to lead from the individual reference result to the individual test result, the probability includes a probability term for artifact reporting occurrence;

when artifact reporting is one of the types of spurious information considered and where artifact reporting must not occur to lead from the individual reference result to the individual test result, the probability includes a probability term for artifact reporting non-occurrence;

combining the expressions of probability that the individual reference result could lead to the individual test result for the plurality of loci to give a likelihood ratio of the probability that the test sample matches the reference sample; and, determining whether or not the DNA of the test sample originated from one or more of the known individuals based on the likelihood ratio.

15. A non-transitory computer-readable medium comprising computer code configured to perform a computer-implemented method of comparing one or more reference samples of DNA from known individuals with a test sample of DNA, the method comprising:

determining the identity of alleles present at a plurality of loci in the DNA of the test sample to give a plurality of respective individual test results;

comparing each of the plurality of individual test results against a corresponding individual reference result of the one or more reference samples for the respective loci, the corresponding individual reference result comprising the identities of alleles present in the DNA of one of the reference samples at the same respective locus as the individual test result, the comparison involving an expression of the probability that the individual reference result for that locus could lead by various possible routes to the individual test result for the locus, the possible routes to the individual test result including routes where spurious information contributes to the individual test result, the expression of the probability is a probability function that includes more than one of a probability that contamination may occur, a probability that stutter may occur, a probability that allele dropout may occur, and a probability that artefact reporting may occur;

when contamination is one of the types of spurious information considered and where contamination is necessary to lead from the individual reference result to the individual test result, the probability includes a probability term for spurious allele occurrence;

when contamination is one of the types of spurious information considered and where contamination must not occur to lead from the individual reference result to the individual test result, the probability includes a probability term for spurious allele non-occurrence;

when stutter is one of the types of spurious information considered and where stutter is necessary to lead from the individual reference result to the individual test result, the probability includes a probability term for stutter occurrence;

when stutter is one of the types of spurious information considered and where stutter must not occur to lead from the individual reference result to the individual test result, the probability includes a probability term for stutter non-occurrence;

when allele dropout is one of the types of spurious information considered and where allele dropout is necessary to lead from the individual reference result to the individual test result, the probability includes a probability term for allele dropout occurrence;

when allele dropout is one of the types of spurious information considered and where allele dropout must not occur to lead from the individual reference result to the individual test result, the probability includes a probability term for allele dropout non-occurrence;

when artifact reporting is one of the types of spurious information considered and where artifact reporting is necessary to lead from the individual reference result to the individual test result, the probability includes a probability term for artifact reporting occurrence;

when artifact reporting is one of the types of spurious information considered and where artifact reporting must not occur to lead from the individual reference result to the individual test result, the probability includes a probability term for artifact reporting non-occurrence;

combining the expressions of probability that the individual reference result could lead to the individual test result for the plurality of loci to give a likelihood ratio of the probability that the test sample matches the reference sample; and, determining whether or not the DNA of the test sample originated from one or more of the known individuals based on the likelihood ratio.

* * * * *